United States Patent
Andersson et al.

(10) Patent No.: US 6,289,286 B1
(45) Date of Patent: Sep. 11, 2001

(54) SURFACE REGENERATION OF BIOSENSORS AND CHARACTERIZATION OF BIOMOLECULES ASSOCIATED THEREWITH

(75) Inventors: Karl Andersson; Markku Hämäläinen; Magnus Malmqvist; Håkan E. Roos, all of Uppsala (SE)

(73) Assignee: Biacore AB, Uppsala (SE)

(*) Notice: Subject to any disclaimer, the term of this patent is extended or adjusted under 35 U.S.C. 154(b) by 0 days.

(21) Appl. No.: 09/087,402

(22) Filed: May 29, 1998

(51) Int. Cl.[7] .................................................. G01N 33/48

(52) U.S. Cl. .................... 702/19; 436/501; 436/538; 435/7.1; 210/618; 210/635

(58) Field of Search ................................. 702/19, 20, 21; 435/4, 7.1; 436/501–503, 538, 547, 820; 210/614–618, 635

(56) References Cited

U.S. PATENT DOCUMENTS

| | | | |
|---|---|---|---|
| 4,236,893 | * 12/1980 | Rice | 436/531 |
| 4,271,140 | * 6/1981 | Bunting | 436/503 |
| 4,735,906 | * 4/1988 | Bastiaans | 436/501 |
| 4,963,263 | 10/1990 | Kauvar | 210/635 |
| 5,133,866 | 7/1992 | Kauvar | 210/635 |
| 5,409,611 | 4/1995 | Kauvar | 210/635 |
| 5,567,317 | 10/1996 | Kauvar | 210/635 |
| 5,587,293 | * 12/1996 | Kauvar et al. | 435/7.21 |

FOREIGN PATENT DOCUMENTS

| | | |
|---|---|---|
| 2193318 | 6/1997 | (CA) . |
| 781 999 A1 | 7/1997 | (EP) . |
| 2 270 976 A | 3/1994 | (GB) . |
| 63229359 | 9/1988 | (JP) . |
| WO 98/26288 | 6/1998 | (WO) . |

OTHER PUBLICATIONS

Andersson et al., "Identification and Optimization of Regeneration Conditions for Affinity–Based Biosensor Assays. A Multivariate Cocktail Approach," *Anal. Chem.* 71(13):2475–2481, 1999.

Brigham–Burke and O'Shannessy, "A Micro–Scale Method Employing Surface Plasmon Resonance Detection for the Determination of Conditions for Immunoaffinity Chromatography of Proteins," *Chromatographia* 35:45–49, 1993.

Brigham et al., "Detection of Receptor–Ligand Interactions Using Surface Plasmon Resonance: Model Studies Employing the HIV–1 gp120/CD4 Interaction," *Analytical Biochemistry* 205:125–131, 1992.

Casasnovas, "Kinetics and Thermodynamics of Virus Binding to Receptor," *Journal of Biological Chemistry* 270:13216–24, 1995.

Corr et al., "H–2D[d] Exploits f Four Residue Peptide Binding Motif," *Journal of Experimental Medicine* 178:1877–92, 1993.

Cunningham and Wells, "Comparison of a Structural and Functional Epitope," *J. Mol. Biol.* 234:554–563, 1993.

End et al., "A Biosensor Approach to Probe the Structure and Function of the p85α Subunit of the Phosphatidylinositol 3–Kinase Complex," *Journal of Biological Chemistry* 268:10066–75, 1993.

(List continued on next page.)

*Primary Examiner*—Patrick Assouad
*Assistant Examiner*—Bryan Bui
(74) *Attorney, Agent, or Firm*—Seed Intellectual Property Law Group PLLC

(57) ABSTRACT

Surface regeneration of affinity biosensors and characterization of biomolecules associated therewith by multivariate technique employing cocktails of regeneration agents to optimize regeneration of biosensor surface and/or characterize biomolecules associated therewith. Kits and stock solutions for use in the context of this invention, as well as associated computer algorithms are also disclosed.

48 Claims, 13 Drawing Sheets

OTHER PUBLICATIONS

Karlsson and Fält, "Experimental design for kinetic analysis of protein–protein interactions with surface plasmon resonance biosensors," *J. Immunol. Meth.* 200:121–133, 1997.

Karlsson et al., *Structures of Anitgens*, M. H. V. Van Regenmortel (Editor), CRC Press, Boca Raton, 1992, vol. 1., Chapter 7, "Measurement of Antibody Affinity," pp. 127–148.

Lemmon et al., "Independent Binding of Peptide Ligands to the SH2 and SH3 Domains of Grb2," *Journal Of Biological Chemistry* 269:31653–58, 1994.

Ma et al., "Amino–terminal Conserved Region in Proteinase Inhibitor Domain of Calpastatin Potentiates Its Calpain Inihibitory Activity by Interacting with Calmodulin–like Domain of the Proteinase," *Journal of Biological Chemistry* 39:24430–36, 1994.

Malmborg et al., "Real Time Analysis of Antibody–Antigen Reaction Kinetics," *Scandinavian Journal of Immunology* 35:643–50, 1992.

Minunni Mascini, "Detection Of Pesticide In Drinking Water Using Real–Time Biospecific Interaction Analysis (BIA)," *Analytical Letters* 26(7):1441–60, 1993.

Morelock et al., "Determination of Receptor–Ligand Kinetic and Equilibrium Binding Constants using Surface Plasmon Resonance: Application to the lck SH2 Domain and Phosphotyrosyl Peptides," *Journal of Medicinal Chemistry* 38:1309–18, 1995.

Myszka, "Kinetic analysis of macromolecular interactions using surface plasmon resonance biosensors," *Current Opinion In Biotechnology* 8:50–57, 1997.

Nakamura et al., "A Plasma–Polymerized Film for Surface Plasmon Resonance Immunosensing," *Anal. Chem.* 69:4649–4652, 1997.

Okazaki et al., "Determination of the Interactions between Lectins and Glycoproteins by Surface Plasmon Resonance," *Journal of Molecular Recognition* 8:95–99, 1995.

Persson et al., "Analysis of Oligonucleotide Probe Affinities Using Surface Plasmon Resonance: A Means for Mutational Scanning," *Analytical Biochemistry* 246:34–44, 1997.

Sternesjö et al., "Determination of Sulfamethazine Residues in Milk by a Surface Plasmon Resonance–Based Biosensor Assay," *Analytical Biochemistry* 226:175–81, 1995.

Stitt et al., "The Anticoagulation Factor Protein S and Its Relative, Gas6, Are Ligands for the Tyro 3/Axl Family of Receptor Tyrosine Kinases," *Cell* 80:661–70, 1995.

Tanchou et al., "Monoclonal Antibody–Mediated Inhibition of RNA Binding and Annealing Activities of HIV Type 1 Nucleocapsid Protein," *AIDS Research and Human Retroviruses* 10(8):983–93, 1994.

VanCott et al., "Characterization of a soluble, oligomeric HIV–1 gp160 protein as a potential immunogen,"*Journal of Immunological Methods* 183:103–17, 1995.

Ward et al., "Binding Of Anti–Human–Interleukin–6 Monoclonal Antibodies To Synthetic Peptides Of Human Interleukin-6 Studied Using Surface Plasmon Resonance," *Biochemistry International* 26(3):559–565, 1992.

* cited by examiner

US 6,289,286 B1

SURFACE REGENERATION OF BIOSENSORS AND CHARACTERIZATION OF BIOMOLECULES ASSOCIATED THEREWITH

TECHNICAL FIELD

This invention relates generally to surface regeneration of affinity biosensors and characterization of biomolecules associated therewith and, more particularly, to use of a multivariate technique employing cocktails of regeneration agents to optimize regeneration of the surface of a biosensor and characterize biomolecules associated therewith, as well as related regeneration kits, reagents and algorithms for the same.

BACKGROUND OF THE INVENTION

A variety of analytical techniques are used to characterize interactions between molecules, particularly in the context of assays directed to the detection and interaction of biomolecules. For example, antibody-antigen interactions are of fundamental importance in many fields, including biology, immunology and pharmacology. In this context, many analytical techniques involve binding of a "ligand" (such as an antibody) to a solid support, followed by contacting the ligand with an "analyte" (such as an antigen). Following contact of the ligand and analyte, some characteristic is measured which is indicative of the interaction, such as the ability of the ligand to bind the analyte. After measurement of the interaction, the ligand-analyte pair must be disrupted in order to "regenerate" free ligand for a further analytical measurement.

A number of techniques have been employed to regenerate surface-bound ligands. Most commonly, regeneration involves a series of trial and error attempts to remove the analyte from the ligand, while minimizing loss of ligand from the solid support. Care must also be taken not to use a regeneration solution that is too aggressive in order to avoid partial or complete loss of ligand activity. Furthermore, regeneration must not influence the ligand with regard to subsequent measurements, otherwise results from assay-to-assay will not be truly comparable. These problems may be avoided by simply discarding the solid support after each assay. However, this is undesirable since generation of the solid support having bound ligand can be both costly and time consuming, and very often the researcher has only limited quantities of the ligand and/or solid support. Accordingly, improved techniques for regenerating such surfaces are desired.

The need to effectively regenerate a solid surface may be illustrated in the context of biosensors which use surface plasmon resonance (SPR) to monitor the interactions between an analyte and a ligand bound to a solid support. In this regard, a representative class of biosensor instrumentation is sold by Biacore AB (Uppsala, Sweden) under the trade name BIAcore® (hereinafter referred to as "the BIAcore instrument"). The BIAcore instrument includes a light emitting diode, a sensor chip covered with a thin gold film, an integrated fluid cartridge and photo detector. Incoming light from the diode is reflected in the gold film and detected by the photo detector. At a certain angle of incidence ("the SPR angle"), a surface plasmon wave is set up in the gold layer, which is detected as an intensity loss or "dip" in the reflected light.

The SPR angle depends on the refractive index of the medium close to the gold layer. In the BIAcore instrument, dextran is typically coupled to the gold surface, and a ligand is bound to the dextran layer. The analyte of interest is injected in solution form onto the sensor surface through a fluid cartridge. Since the refractive index in the proximity of the gold film depends upon (1) the refractive index of the solution (which is constant) and, (2) the amount of material bound to the surface, the interaction between the bound ligand and analyte can be monitored as a function of the change in SPR angle.

A typical output from the BIAcore instrument is a "sensorgram," which is a plot of response (measured in "resonance units" or "RU") as a function of time. An increase of 1000 RU corresponds to an increase of mass on the sensor surface of approximately 1 ng/mm$^2$. As sample containing an analyte contacts the sensor surface, the ligand bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicted on the sensorgram by a drop in RU over time as analyte dissociates from the surface-bound ligand.

A representative sensorgram for the BIAcore instrument is presented in FIG. 1, which depicts an antibody surface interacting with analyte in a sample. During sample injection, an increase in signal is observed due to binding of the analyte (i.e., association) to a steady state condition where the resonance signal plateaus. At the end of sample injection, the sample is replaced with a continuous flow of buffer and decrease in signal reflects the dissociation of analyte from the surface. The slope of the association/dissociation curves provide valuable information regarding the reaction kinetics, and the height of the resonance signal represents surface concentration (i.e., the response resulting from an interaction is related to the change in mass concentration on the surface). While dissociation will naturally tend to regenerate some portion of the sensor surface, only a very small portion of the sensor surface is typically regenerated in this manner, especially when their is a strong interaction between the ligand and analyte. Thus, some further regeneration step is often needed in order to effectively remove analyte from the sensor surface and ready the surface for contact with a new sample.

Numerous articles have been published directed to the use of the BIAcore instrument in the analysis of biomolecular interactions. In these articles, researchers have reported a variety of regeneration agents and techniques for regenerating the sensor surface prior to contact with a new sample. In general, these articles had main goals other than surface regeneration; however, three papers discussed systematic investigations of regeneration practices concerning antibody-antigen assays (Brigham & O'Shannessy, *Chromatographia* 35:45–49, 1993; Brigham et al., *Analytical Biochemisty* 205:125–131, 1992; Minunni et al., *Analytical Letters* 26:1441–60, 1992), with perhaps the most extensive treatment being that of Burke & O'Shannesy (1993). In that reference, a sCR1-MAb YZ1 system was regenerated using various regeneration agents. The results of this study indicated that, among several common regeneration agents, only a few had a high regeneration effect for the sCR1-MAb YZ1 system. The authors reported that the choice of acid can be more important than the choice of pH (e.g., 0.1M phosphoric acid, pH 1.3, worked better than 0.1M HCl, pH 1.0), and that combinations of agents in some cases are favorable (e.g., 50% ethyleneglycol/0.1M triethylamine, pH 10.5, was more favorable than 0.1M triethylamine, pH 10.5).

More generally, the above-noted articles disclose that various classes of ligand-analyte systems may be regenerated under the following conditions:

Antibody-antigen assays—to varying degrees with hydrochloric acid (HCl) of different concentrations (Malmborg et al, *Scandinavial Journal of Immunology* 35:643–50, 1992; Ward et al., *Biochemistry International* 26:559–65, 1992) or with weaker acids, typically phosphoric or formic (Corr et al., *Journal of Experimental Medicine* 178:1877–92, 1993; VanCott et al., *Journal of Immunological Methods* 183:103–17, 1995), or with detergent or chaotropic solutions (Tanchou et al., *AIDS Research and Human Retroviruses*, 10:983–93 1994; End et al., *Journal of Biological Chemistry* 268:10066–75, 1993);

Receptor-transmitter assays—with acids (Morelock et al., *Journal of Medicinal Chemistry* 38:1309–18, 1995), bases (Lemmon et al., *Journal of Biological Chemistry* 269:31653–58, 1994), under chaotropic conditions and high ion strength (Stitt et al., *Cell* 80:661–70, 1995), or under natural dissociation conditions (Ma et al., *Journal of Biological Chemistry* 39:24430–36, 1994);

Assays containing DNA—under very mild regeneration conditions using detergents, EDTA, or under natural dissociation conditions (Cheskis et al., *Molecular Endocrinology* 1996; Casasnovas *Journal of Biological Chemistry* 270:13216–24, 1995); and Assays containing glycoproteins—under acid conditions or using sugar solutions (Okazaki et al., *Journal of Molecular Recognition* 8:95–99 1995).

While these articles disclose a variety of regeneration techniques, those techniques are system dependent and are not particularly effective beyond the parameters of the specific system reported in each paper. Thus, anytime a researcher investigates a new ligand-analyte system, a great deal of time and effort may be spent identifying regeneration conditions suitable for the system at hand, often with varying degrees of success. Accordingly, there is a need in the art for improved techniques for regenerating the surface of an affinity biosensor.

There is also a need in the art for techniques to characterize the analyte and/or ligand associated with the surface of an affinity biosensor. Such characterization can occur either prior to the regeneration of the biosensor surface (e.g., during association or dissociation) or can occur during regeneration. Further, the ability to predict structure-activity relationships ("SAR") has become an important goal in a variety of fields. For example, as the number of known protein structures has increased, researchers have tried, with limited success, to predict SAR for such proteins. In the context of monoclonal antibodies, one goal has been to design a MAb that binds specifically to a given antigen, in advance of laboratory experiments. Accordingly, a need exists for techniques that can predict SAR for new analytes and/or ligands, such as proteins, and thus characterize their activity in advance of laboratory analysis of the same.

There is also a need to characterize analytes and/or ligands with respect to changing chemical environments. For example, in developing quantitative assays for determination of vitamin concentration in food, researchers are often interested in knowing how sensitive a specific molecule, typically a MAb, is to variations in its chemical environment. An aqueous solution having a known amount of vitamin, for example, may be more sensitive than a crude sample (e.g., infant formulas, cereals, etc.) having the same concentration of vitamin. Therefore, the measured concentration of vitamin from the crude sample may be different than its true concentration. Similarly, when determining drug and/or hormone residues in animals (e.g., in urine), researchers are also often interested in knowing how sensitive a specific molecule is to variations in its chemical environment. Accordingly, a need exists for techniques that can predict the performance of a specific molecule in a crude sample. Such techniques may also be useful in developing quantitative assays.

Furthermore, there is also a need in the art to detect and characterize minor structural differences in, for example, proteins. Researchers often desire to verify that manufactured proteins have their expected structures, and are not point-mutated or post modified (i.e., by substitutions by carbohydrates, fatty acids, etc.). Accordingly, a need exists for methods useful for detecting minor structural differences in proteins.

The present invention fulfills these needs, and provides further related advantages.

SUMMARY OF THE INVENTION

In brief, the present invention is directed to regeneration of a biosensor surface, particular with regard to identification and selection of regeneration agents and conditions for use of the same, as well as to the characterization of biomolecules associated with the biosensor surface. Reagent kits and methods are also disclosed for use within the context of this invention.

In one embodiment, a method is disclosed for selecting an optimized regeneration solution for the regeneration of a biosensor surface having a surface-bound ligand and an analyte associated with the ligand. The method comprises the steps of:

(a) sequentially contacting the biosensor surface with each of a plurality of first regeneration cocktails, wherein each of said first regeneration cocktails is an aqueous solution comprising at least one acidic, basic, ionic, organic, detergent or chelating stock solution, and wherein at least one of said first regeneration cocktails comprises a mixture of at least two of said stock solutions;

(b) measuring the regeneration effect for each of said plurality of first regeneration cocktails to determine which of said plurality of first regeneration cocktails have the highest measured regeneration effect;

(c) selecting at least two different stock solutions present in said plurality of first regeneration cocktails having the highest measured regeneration effect;

(d) combining said at least two different stock solutions in various ratios to generate a plurality of second regeneration cocktails;

(e) sequentially contacting the biosenor surface with each of said plurality of second regeneration cocktails; and (f) determining the regeneration effect of each of said plurality of second regeneration cocktails and therefrom identifying a second regeneration cocktail as the optimized regeneration solution.

In a further aspect of this embodiment, the method further comprising, after step (f), the following additional steps:

(g) combining said at least two different stock solutions in different ratios than step (d) to generate a plurality of third regeneration cocktails;

(h) sequentially contacting the biosensor surface with each of aid plurality of third regeneration cocktails; and (i) determining the regeneration effect of each of said plurality of third regeneration cocktails and therefrom identifying a third regeneration cocktail as the optimized regeneration solution.

The above steps may be repeated until the optimized regeneration olution is identified.

In another embodiment of this invention, a reagent kit is disclosed containing at least two different stock solutions for use within the above method. Preferably, all six different stock solutions are present in the reagent kit—that is, an acidic stock solution, a basic stock solution, an ionic stock solution, an organic stock solution, a detergent stock solution, and a chelating stock solution.

In still a further embodiment, a computer system is disclosed for selecting an optimized regeneration solution for the regeneration of a biosensor surface having a surface-bound ligand and an analyte associated with the ligand. The computer systems performs the following steps:

(a) instructing a device to combine a series of stock solutions in various ratios to generate a plurality of first regeneration cocktails;

(b) sequentially controlling the device to contact the biosensor surface with each of said plurality of first regeneration cocktails;

(c) determining the regeneration effect of each of said first regeneration cocktails on the biosensor surface based on measurements received from the device;

(d) selecting at least two different stock solutions having the highest regeneration effect;

(e) instructing the device to combine a subset of said at least two different stock solutions in varying ratios to generate a plurality of second regeneration cocktails;

(f) sequentially controlling the device to contact the biosenor surface with each of said second regeneration cocktails; and (g) determining the regeneration effect of each of said second regeneration cocktails based on measurements received from the device, and therefrom identifying a second regeneration cocktail as the optimized regeneration solution.

In a further embodiment, a method is disclosed for characterizing a ligand and/or analyte associated with a biosensor surface, comprising the steps of:

(a) sequentially contacting the biosensor surface having a surface-bound ligand with each of a plurality of characterization solutions, wherein each of said characterization solutions is an aqueous solution comprising at least one acidic, basic, ionic, organic, detergent or chelating solution;

(b) introducing the analyte into each of said plurality of characterization solutions so as to interact the analyte with the surface-bound ligand;

(c) measuring at least one of the association rate, surface-bound analyte concentration, and dissociation rate of the analyte-ligand interaction for each of said plurality of characterization solutions; and (d) characterizing the ligand and/or analyte associated with the biosensor surface based on at least one of the association rate, surface-bound analyte concentration, dissociation rate, and regeneration effect of the analyte-ligand interaction for each of said plurality of characterization solutions.

In a further aspect of this embodiment, the method further comprises, after step (d), the following additional step:

(e) comparing the characterization of the ligand and/or analyte associated with the biosensor surface with a set of predetermined characterizations of other test molecules, and thereby predicting the activity of the ligand and/or analyte associated with the biosensor surface.

In yet a further embodiment, a computer-readable medium is disclosed containing the instructions for performing the above methods.

These and other aspects of this invention will be evident upon reference to the attached drawings and following detailed description. To this end, various references are cited throughout this application to further illustrate specific aspects of this invention. Such documents are each incorporated herein by reference in their entirety.

DETAILED DESCRIPTION OF THE INVENTION

Figure 1:
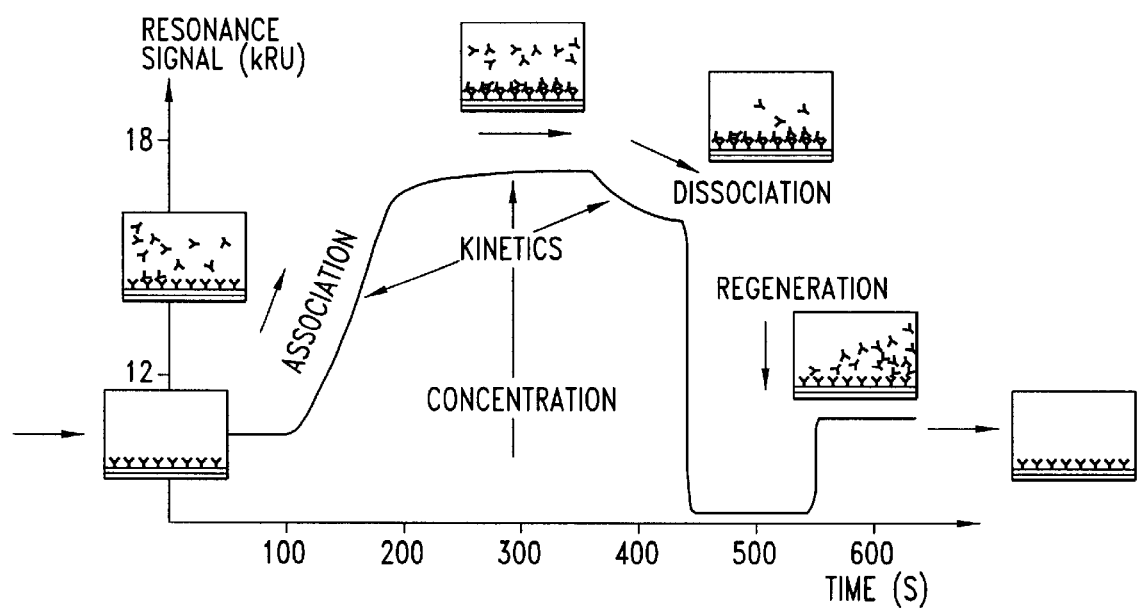
FIG. 1 is a representative sensorgram illustrating association, steady-state, dissociation and regeneration of a biosensor surface.

As mentioned above, this invention is directed to regeneration of a biosensor surface, particular with regard to identification and selection of regeneration agents and conditions for use of the same, as well as to the characterization of biomolecules associated with a biosensor surface. This invention also provides reagent kits for use within the context of this invention, as well as related algorithms and computer-readable mediums containing the same.

In one embodiment, a method is disclosed for selecting an optimized regeneration solution for regenerating a biosensor surface (i.e., a regeneration identification and optimization (RO) protocol) having a surface-bound ligand and an analyte associated therewith. The analyte is typically bound (i.e., associated) to the ligand by non-covalent forces (e.g., electrostatic and Lewis acid-Lewis base forces). Suitable biosensor surfaces include a wide number of biosensors, particularly affinity-based biosensors. Such biosensors often have a binding or interaction partner bound to the surface which is to be contacted with the sample of interest. In the context of this invention, the agent bound to the surface of the biosensor is referred to as a "ligand," while the interactant in solution (e.g., the sample) is called the "analyte."

As used herein, the terms "ligand" and "analyte" are to be construed broadly, and encompass a wide variety of molecules ranging from small molecules to large proteins, as well as a variety of interaction pairs. For example, representative ligands include, but are not limited to, the agents listed below (representative analyte interaction partners are parenthetically identified): antigen (specific antibody), antibody (antigen), hormone (hormone receptor), hormone receptor (hormone), polynucleotide (complementary polynucleotide), avidin/streptavidin (biotin), biotin (avidin/streptavidin), enzyme (enzyme substrate or inhibitor), enzyme substrate or inhibitor (enzyme), lectins (specific carboxyhydrate), specific carboxyhydrate (lectins), lipids (lipid binding proteins or membrane-associated proteins), lipid binding proteins or membrane-associated proteins (lipids), polynucleotides (polynucleotide binding proteins), polynucleotide binding proteins (polynucleotides), receptor (transmitter), transmitter (receptor), drug (target), target (drug), as well as more general types of interactions such as protein (protein), protein (polynucleotide), polynucleotide (protein), DNA (DNA), DNA (RNA), and RNA (DNA) interactions.

The biosensors of this invention are used in conjunction with a detection device which may employ a variety of detection methods. Typically, such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging, such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers. While the present invention is hereinafter illustrated in the context of SPR spectroscopy, it is to be understood that the invention is not limited in this manner.

As mentioned above, the BIAcore instrument (Biacore AB, Uppsala, Sweden) is an SPR-based, affinity biosensor system which is particularly useful for determining affinity and kinetics of interactions between two or more biomolecules (Karlsson et al., *Structures of Antigens*, M. H. V. Van Regenmortal (Editor), vol. 1., chap. 7, pp. 127–148, CRC Press, 1992; Karlsson et al., *J. Immunol. Meth.* 200:121–133, 1997; Myszka, *Current Opinion in Biotechnology* 8:50–57, 1997), receptor-ligand interactions (Cunningham et al., *J. Mol. Biol.* 234:554–563, 1993), and hybridizations (Persson et al., *Anal. Biochem.* 246:34–44, 1997). The BIAcore instrument is also used for quantitative analysis using antibodies as a specific reagent (Sternesjö et al., *Analytical Biochemistry* 226:175–81, 1995). The vast majority of such methods require regeneration of the biosensor surface before a measurement can be repeated. Thus, optimization of regeneration conditions is of both general and specific interest.

In the BIAcore instrument, the biosensor surface is preferably regenerated with a regeneration agent that does not influence the bound ligand in any permanent sense. Otherwise the system characteristics will change from measurement to measurement, which may result in data that is not truly comparable. Specifically, for kinetic assays, the model parameters may have different true values for each measurement, whereas for quantitative assays the calibration may become less valid because of a baseline shift during consequent measurements.

The present invention overcomes these problems, and provides further related advantages, by employing a small library of "stock solutions" that simplify identification and optimization of regeneration conditions for biosensor surfaces. The stock solutions of the present invention constitute different chemical properties which, either alone or in some combination, are representative of the vast majority of the regeneration agents presently employed for surface regeneration. Of these chemical properties, acid, base, ion strength, detergent, organic and chelating agents have been found to be sufficient in the context of this invention. Thus, the library of the present invention is made in the form of six stock solutions representing each of these properties. Each stock solution typically contains several compounds with similar main properties, but with differences in molecular structure, pKa, etc. In one embodiment, the regeneration effects of predefined mixes of the six stock solutions and water in various combinations are initially tested. In another embodiment, the regeneration effects of mixes of the six stock solutions with or without added water in various combinations are initially tested. Such mixtures of stock solutions, either with a single stock solution and water, or with at least two different stock solutions with or without added water, are referred to herein as "regeneration cocktails."

In order to determine the regenerative effects for each of the stock solutions that comprise the corresponding regeneration cocktails, a structured experimental design has been developed. More specifically, a multivariate approach or protocol is employed for identifying and optimizing the regeneration conditions for a particular biosensor surface. Such a structured experimental design forces the parameters under investigation, namely the six stock solutions, to vary in an uncorrelated manner. As a result, it is possible to estimate the degree of importance of each parameter. Moreover, a structured experimental design also allows conclusions to be drawn that are typically more reliable than from experiments where the parameters are allowed to vary only one at a time (Haaland, P. D. *Experimental Design in Biotechnology*; Marcel Dekker: New York, 1989; Box; Hunter; Hunter *Statistics for Experimenters*; John Wiley & Sons, 1978). As such, the experiments of the present invention are designed with focus on ease-of-use rather than on getting maximal information from a given number of experiments. Thus, the approach of this invention results in experimental data that can be reliably evaluated without the need for any sophisticated mathematical or statistical analysis.

More specifically, in the practice of the present invention, a biosensor surface is sequentially contacted with each of a plurality of first regeneration cocktails made from the library of six stock solutions. As used herein, a "plurality" of first regeneration cocktails means at least two, typically at least eight, and preferably at least 18. Such first regeneration cocktails are aqueous solutions comprising at least one acidic, basic, ionic, organic, detergent, or chelating stock solutions. Further, in the practice of the present invention at least one of the first regeneration cocktails comprises a mixture of at least two different stock solutions selected from the above list. For purposes of convenience, the stock solutions of the present invention are abbreviated as follows: A (acidic), B (basic), I (ionic), O (organic), D (detergent) and C (chelating).

In addition, it should also be understood that each of the first regeneration cocktails comprise an aqueous mixture of water ("w") and at least one, and typically one or two, and possibly three or more stock solutions of the present invention. Representative first regeneration cocktails of this invention that contain one or two stock solutions are listed in Table 1, while representative first regeneration cocktails that contain three stock solutions are listed in Table 2, wherein each component is represented as an equal volume component. For example, the first regeneration cocktail "Aww" represents one volume of stock solution A mixed with two volumes of water, whereas "BAw" represents a mixture of one volume of stock solution B, one volume of stock solution A, and one volume of water. However, other ratios of water may also be used. To this end, water may be present in each of the first regeneration cocktails in an amount ranging from 0% to 95% by volume, typically from 20% to 50%, and preferably from 33% to 50%. (Note that first regeneration cocktails corresponding to "BIw" and "BOw" are not depicted as these mixtures may form precipitates, while the first regeneration cocktail corresponding to "IOw" is not depicted as this mixture may be too aggressive.)

TABLE 1

Representative First Regeneration Cocktails Containing One Or Two Stock Solutions

| Aww | Bww | Iww | Oww | Dww | Cww |
|---|---|---|---|---|---|
| BAw | BDw | BCw | AIw | AOw | ADw |
| ACw | IDw | ICw | DOw | DCw | OCw |

TABLE 2

Representative First Regeneration Cocktails Containing Three Stock Solutions

| ABIw | ABDw | ABCw | AIDw | AICw | ADOw |
|---|---|---|---|---|---|
| ADCw | AOCw | BDOw | BOCw | IDCw | DOCw |

As stated above, the stock solutions of the present invention are aqueous solutions comprising at least one acidic, basic, ionic, organic, detergent or chelating component. Typically, each stock solution contains a combination of two or more components of like kind (with the exception of the chelating stock solution as discussed below). The concentration of each component within each stock solution is typically high, in some cases approaching saturation. Employing high concentration stock solutions is preferable since it permits a wide range of concentrations following dilution with other stock solutions and/or water. Representative components for each stock solution of the chemical library are discussed further below.

Acidic stock solutions of the present invention comprise one or more acids having dispersed pKs ranging from about 2 up to about 7, and having a pH ranging from 1 up to about 7. Suitable acids in this context include both organic and inorganic acids such as arsenic acid, arsenious acid, o-boric acid, carbonic acid, chromic acid, germanic acid, hyrocyanic acid, hydrofluoric acid, hydrogen sulfide, hydrogen peroide, hypobromus acid, hypochlorous acid, hypoiodous acid, iodic acid, nitrous acid, periodic acid, o-phosphoric acid, phosphorous acid, pyrophosphoric acid, selenic acid, selenious acid, m-silic acid, o-silic acid, sulfuric acid, sulfurous acid, telluric acid, tellurous acid, tetraboric acid, acetic acid, acetoacetic acid, acrylic acid, adipamic acid, adipic acid, d-alanine, allantoin, alloxanic acid, glycine, o-aminobenzoic acid, m-aminobenzoic acid, p-aminobenzoic acid, o-aminobenzsulfonic acid, m-aminobenzsulfonic acid, p-aminobenzsulfonic acid, ainsic acid, o-beta-anisylpropionic acid, m-beta-anisylpropionic acid, p-beta-anisylpropionic acid, ascorbic acid, DL-aspartic acid, barbituric acid, benzoic acid, benzosoulfonic acid, bromoacetic acid, o-bromobenzoic acid, m-bromobenzoic acid, n-butyric acid, iso-butyric acid, cyclopropane-1:1-dicarboxylic acid, DL-cystein, L-cystein, dichloroacetic acid, dichloroacetylacetic acid, 2,3-dichlorophenol, 2,2-dihydroxybenzoic, 2,5-dihydroxybenzoic, 3,4-dihydroxybenzoic, 3,5-dihydroxybenzoic, dihydroxymalic acid, dihydroxytartaric acid, dimethylglycine, dimethylmalic acid, dimethylmalonic acid, dinicotinic acid, 2,4-dinitrophenol, 3,6-dinitrophenol, diphenylacetic acid, ethylbenzoic acid, ethylphenylacetic acid, fluorobenzoic acid, formnic acid, fumaric acid, furancarboxylic acid, furoic acid, cacodylic acid, n-caproic acid, iso-caproic acid, chloroacetic acid, o-chlorobenzoic acid, m-chlorobenzoic acid, p-chlorobenzoic acid, o-chlorobutyric acid, m-chlorobutyric acid, p-chlorobutyric acid, o-chloroinnamic acid, m-chloroinnamic acid, p-chloroinnamic acid, o-chlorophenoxyacetic acid, m-chlorophenoxyacetic acid, p-chlorophenoxyacetic acid, o-chlorophenylacetic acid, m-chlorophenylacetic acid, p-chlorophenylacetic acid, beta-(o-chlorophenyl) propionic acid, beta-(m-chlorophenyl) propionic acid, beta-(p-chlorophenyl) propionic acid, alfa-chloropropinic acid, beta-chloropropionic acid, cis-cinnamic acid, trans-cinnamic acid, citric acid, o-cresol, m-cresol, p-cresol, trans-crotonic acid, cyanoacetic acid, gamma-cyanobutyric acid, o-cyanophenoxyacetic acid, p-cyanophenoxyacetic acid, cyanopropionic acid, cycloheaxane-1:1-dicarboxylic acid, gallic acid, glutamaric acid, glutaric acid, glycerol, glycine, glycol, glycolic acid, heptanoic acid, hexahydrobenzoic acid, hexanoic acid, hippuric acid, histidine, hydroquinone, o-hydroxybenzoic acid, m-hydroxybenzoic acid, p-hydroxybenzoic acid, beta-hydroxybutyric acid, gamma-hydroxybutyric acid, beta-hydroxypropionic acid, gamma-hydroxyquinoline, iodoacetic acid, o-iodobenzoic acid, m-iodobenzoic acid, itaconic acid, lactic acid, lutidinic acid, lysine, maleic acid, malic acid, malonic acid, DL-mandelic acid, mesaconic acid, mesitylenic acid, methyl-o-aminobenzoic acid, methyl-m-aminobenzoic acid, methyl-p-aminobenzoic acid, o-methylcinnamic acid, m-methylcinnamic acid, p-methylcinnamic acid, beta-methylglutaric acid, n-methylglycine, methylmalonic acid, methylsuccinic acid, o-monochlorophenol, m-monochlorophenol, p-monochlorophenol, o-phthalic acid, m-phthalic acid, p-phthalic acid, picric acid, pimelic acid, propionic acid, iso-propylbenzoic acid, 2-pyridinecarboxylic acid, 3-pyridinecarboxylic acid, 4-pyridinecarboxylic acid, pyrocatcchol, quinolinic acid, Resorcinol, Saccarin, suberic acid, succinic acid, sulfanilic acid, naphtalenesulfonic acid, alfa-naphthoic acid, beta-naphthoic acid, alfa-napthol, beta-napthol, nitrobenzene, o-nitrobenzoic acid, m-nitrobenzoic acid, p-nitrobenzoic acid, o-nitrophenol, m-nitrophenol, p-nitrophenol, o-nitrophenylacetic acid, m-nitrophenylacetic acid, p-nitrophenylacetic acid, o-beta nitrophenylpropionic acid, p-beta nitrophenylpropionic acid, nonanic acid, octanic acid, oxalic acid, phenol, phenylacetic acid, o-phenylbenzoic acid, gamma-phenylbutyric acid, alfa-phenylpropionic acid, beta-phenylpropionic acid, alfa-tataric acid, alfa-tartaric acid, meso-tartaric acid, theobromine, terephtalic acid, thioacetic acid, thiophenecarboxylic acid, o-toluic acid, m-toluic acid, p-toluic acid, trichloroacetic acid, trichlorophenol, 2,4,6-trihydroxybenzoic acid, trimethylacetic acid, 2,4,6-trinitrophenol, tryptophan, tyrosine, uric acid, n-valeric acid, iso-valeric acid, veronal, vinylacetic acid, and xanthine. In one embodiment, the acidic stock solution is a mixture of acids comprising oxalic (0.15M), phosphoric (0.15M), formic (0.15M), and malonic acid (0.15M), wherein the mixture contains nearly equal volume portions of each acid adjusted to about pH 5.0 with NaOH.

Basic stock solutions of the present invention comprise one or more bases having dispersed pKs ranging from in excess of 7 up to about 12, and a pH ranging from 7 to 12. Suitable bases include acetamide, acridin, alfa-alanin, gylcyl alanin, methoxy (DL)-alanin, phenyl alanin, allothreonin, n-amylamine, aniline, n-allyl aniline, 4-(p-aminobenzoyl) aniline, 4-benzyl aniline, 2-bromo aniline, 3-bromo aniline, 4-bromo aniline, 4-bromo-N,N,dimethyl aniline, o-chloro aniline, m-chloro aniline, p-chloro aniline, 3-bromo-N,N, dimethyl aniline, 4-bromo-N,N,dimethyl aniline, 3,5-dibromo Aniline, 2,4-dichloro aniline, N,N-diethyl aniline, N,N-dimethyl-3-nitro aniline, N-ethyl aniline, 2-fluoro aniline, 3- fluoro aniline, 4-fluoro aniline, 2-iodo aniline, N-methyl aniline, N-methylthio aniline, 3-nitro aniline, 4-nitro aniline, 2-sulfonic acid aniline, 3-sulfonic acid aniline, 4-sulfonic acid aniline, brucine, 1-amino-3-methyl-butane, 2-amino-4-methyl-butane, 1,4-diamino-butane, n-butylamine, t-butylamine, 4-amino butyric acid, lycyl-2-amino n-butyric acid, cacodylic acid, beta-chlortriethylammonium, cinnoline, codeine, n-butyl-cyclohexanamin, cyclohexanamin, cystin, n-decylamine, diethylamine, diisobutylamine, diisopropylamine, dimethylamine, n-diphenylamine, n-dodecaneamine, d-ephedrine, 1-ephedrine, 1-amino-3-metoxy-ethane, 2-amino ethanole, o-anisidine, m-anisidine, p-anisidine, arginin, asparagin, glycylasparagin, DL-aspartic acid, azetidin, aziridine, 4-aminoazo benzene, 2-aminoethyl benzene, 4-dimethylaminoazo benzene, benzidine, benzimidazole, 2-ethyl benzimidazole, 2-methyl benzimidazole, 2-phenyl benzimidazole, 2-amino benzoic acid, 4-amino benzoic acid, benzylamine, betaine, 2-amino biphenyl, trans-bornylamine, ehtylamine, ethylenediamine, 1-Glutamic acid, alfa-monoethyl glutamic acid, 1-glutamine, 1-glutathione, glycine, n-acetyl glycine, dimethyl glycine, glycyl glycine, glycylglycyl glycine, leucyl glycine, methyl glycine, phenyl glycine, N,n-propyl glycine, tetraglycyl glycine, glycylserine, hexadecanamine, 1-amino heptan, 2-amino-heptan, 2-metylamino heptan, hexadecanamine, hexamethylenediamine, 6-amino hexanoic acid, n-hexylamine, dl-histidine, beta-analyl histidine, imidazol, 2,4-dimethyl imidazol, 1-methyl imidazol, 1-amino indane, 2-amino isobutyric acid, isoleucin, isoquinolin, 1-amino isoquinolin, 7-hydroxy isoquinolin, L-leucin, glycyl leucin, methionin, metylamine, morphine, morpholine, 1-amino-6-hydroxy naphtalene, dimethylamino naphtalene, alfa-naphthylamine, beta-napthylamine, piperazine, 2,5,dimetyl(trans)piperazine, piperidine, 3-acetyl piperidine, 1 -n-butyl piperidine, 1,2-dimethyl piperidine, 1-ethyl piperidine, 1-methyl piperidine, 2,2,6,6, tetramethyl piperidine, 2,2,4-trimethyl piperidine, proline, hydroxyproline, 1-amino-2,2-dimethylpropane, 1,2-diaminopropane, 1,3-diaminopropane, 1,2,3-triaminopropane, 3-amino propanoic acid, propylamine, pteridine, 2-amino-4-hydroxy pteridine, 2-amino-4,6-dihydroxy pteridine, 6-chloro pteridine, 6-hydroxy-4-methyl pteridine, purine, n-methyl alfa-naphtylamine, cis-neobornylamine, nicotine, n-nonylamine, norleucine, octadecanamine, octylamine, omithine, papaverine, 3-amino pentane, 3-amino-3-methyl pentane, n-pentadecylamine, 5-amino pentanoic acid, perimidine, phenanthridine, 1,10-phenanthroline, o-phenetidine, m-phenetidine, p-phenetidine, alfa-picoline, beta-picoline, gamma-picoline, pilocarpine, 6-amino purin, 2-dimethylaminopurine, 8-hydroxy purin, pyrazin, 2-methylpyrazine, methylaminopyrazine, pyrdazine, 2-aminopyrimidine, 2-amino-4,6-dimethylpyrimidine, 2-amino-5-nitro pyrimidine, pyridine, 2-amino pyridine, 4-amino pyridine, 2-benzyl pyridine, 3-bromo pyridine, 3-chloro pyridine, 2,5-diamino pyridine, 2,3-dimethyl pyridine, 2,4-dimethyl pyridine, 2-ethyl pyridine, 2-formyl pyridine, a-hydroxy pyridine, 4-hydroxy pyridine, methoxy pyridine, 4-methylamino pyridine, 2,4,6,trimetyl pyridine, pyrrolidine, 1,2-dimethyl pyrrolidine, n-methyl pyrrolidine, quinazoline, 5-hydroxy quinazoline, quinine, quinoline, 3-amino quinoline, 3-bromo quinoline, 8-carboxy quinoline, 3-hydroxy quinoline, 8-hydroxy quinoline, 8-hydroxy-5-sulfo quinoline, 6-methoxy quinoline, 2-methyl quinoline, 4-methyl quinoline, 5-methyl quinoline, quinoxaline, serine, strychnine, taurine; tetradecaneamin, thiazole, 2-aminothiazole, threonine, o-toluidine, m-toluidine, p-toluidine, 2,4,6-triamino- 1,3,5-triazine, tridecanamine, triethylamine, trimethylamine, tryptophan, tyrosine, urea, valine, ammonium hydroxide, arsenous oxide, beryllium hydroxide, calcium hydroxide, deuteroammonium hydroxide, hydrazine, hydroxylamine, lead hydroxide, silver hydroxide, and zinc hydroxide. In one embodiment, the basic stock solution is a mixture of bases comprising ethanolamine (0.20M), sodium phosphate (0.20M), piperazin (0.20M), and glycine (0.20M), wherein the mixture contains nearly equal volume portions of each base adjusted to about pH9.0.

Ionic stock solutions of the present invention comprise a mixture of at least two ionic compounds. Suitable ions of the at least two ionic compounds include $PO_4^{3-}$, $SO_4^{2-}$, $CH_3COO-$, $Br-$, $NO_3-$, $NO_2-$, $ClO_4-$, $Cl-$, $F-$, $I-$, $CF_3COO-$, $SCN-$, $Cl_3COO-$, $CCl_3COO-$, $(CH_3)_4N^+$, $NH_4^+$, $Rb^+$, $K^+$, $Na^+$, $Cs^+$, $Li^+$, $Mg^{2+}$, $Ca^{2+}$, $Sr^{2+}$, and $Ba^{2+}$. Such ions may be generated by adding water to a suitable precursor or salt, such as potassium thiocyanate, magnesium chloride, urea, guanidine HCl, sodium chloride, potassium chloride, ammonium chloride, or lithium chloride. In one embodiment, the ionic stock solution comprises a mixture of potassium thiocyanate (0.46M), magnesium chloride (1.83M), urea (0.92M), and guanidine HCl (1.83M).

Organic stock solutions of the present invention comprise a mixture of at least two organic solvents. Suitable organic solvents include DMSO, formamide, ethanol, acetonitrile, 1-butanol, acetone, methyl acetate, dichloroethane, chloroform, methyl alcohol, tetrahydrofuiran, n-hexane, diisopropyl ether, ethyl acetate, ethyl alcohol, butanone, n-hexane, 2-propanol, 1,2-dichloroethane, flourobenzene, acetone, trichloroethylene, triethylamine, 1-propanol, butyronitrile, 2-butanol, nitromethane, dioxane, 2,2- dimethylpropanole, 3-pentanone, piperazine, 3-propanol, pyridin, 1-butanol, acetic acid, 2-metoxy ethanol, 3-methyl-1-butanol, chlorobenzene, acetic anhydride, dimethylformamide, methoxybenzene, methylbutylketone, bromobenzene, 1-hexanol, n-methyl formamide, aniline, iodobenzene, glycol, phenyl acetate, n-methyl formamide, benzyl alcohol, formamide, nitrophenol, diethyleneglycol, diphenylether, sulfolan, diethylether, methylene chloride, carbon disulfide, carbon tetrachloride, benzene, acetonitrile, toluene, dibutyl ether, mesitylen (e.g., dimethylbenzene), ortho-dichlorobenzene, and benzonitrile. In one embodiment, the organic stock solution comprises nearly equal volume portions of DMSO, formamide, ethanol, acetonitrile, and 1-butanol.

Detergent stock solutions of the present invention comprise a mixture of at least two detergent agents such as anionic detergents, cationic detergents, zwitterionic detergents, and nonionic detergents. In one embodiment, the detergent stock solution comprises CHAPS (0.3% (w/w)), Zwittergent 3–12 (0.3% (w/w)), Tween 80 (0.3% (v/v)), Tween 20 (0.3% (v/v)), and Triton X-100 (0.3% (v/v)) (commercially available from Sigma).

Chelating stock solutions of the present invention comprise at least one chelating agent including EDTA, EGTA, NTA, DCYTA, GLEDTA, ETHEDTA, IDA, Ktyptand 222B, Klyptofix® 221, Kryptofix® 222, and crown ethers (commercially available from Fluka). In one embodiment, the chelating stock solution comprises a 20 mM EDTA solution.

For purposes of illustration, components for each of six representative stock solutions of the present invention are disclosed in Table 3.

TABLE 3

Representative Stock Solutions

| Acidic | Basic | Ionic | Organic | Detergent | Chelating |
|--------|-------|-------|---------|-----------|-----------|
| oxalic | ethanol-amine | KSCN | DMSO | CHAPS | EDTA |
| phos-phoric | Na3PO4 | MgC12 | formamide | Zwittergent | |
| formic | piperazine | urea | ethanol | tween 80 | |
| malonic | glycine | guanidine | acetoni-trile | tween 20 | |
| | | | 1-butanol | triton X-100 | |

In the practice of the present invention a biosensor surface (having a surface-bound ligand and an analyte associated therewith) is sequentially contacted with each of a plurality of first regeneration cocktails, wherein each of the first regeneration cocktails is an aqueous solution comprising at least one acidic, basic, ionic, organic, detergent or chelating stock solution as disclosed above, and wherein at least one of the first regeneration cocktails comprises a mixture of at least two of the stock solutions. For example, in the context of the BIAcore instrument, a plurality of first regeneration cocktails comprising various combinations of the stock solutions and/or water are sequentially introduced into the running buffer so as to come into contact with the biosensor surface to be regenerated.

In one embodiment, each regeneration cocktail is introduced into the running buffer of the BIAcore instrument (e.g., in random order) by a controlled injection of 30 second duration (flow 20 μl/min) into an associated portal. Upon contacting the biosensor surface with each of the plurality of first regeneration cocktails, the regeneration effect for each of the cocktails is measured as the percentage loss of analyte due to the cocktail injection. As used herein, the "regeneration effect" ($R_e$) is calculated by the following Equation (1):

$$R_e = \{(\text{Analyte loss})/(\text{Analyte level})\} \times 100 \quad (1)$$

Based on these measurements, the first regeneration cocktails having the highest regeneration effect are identified. For example, the $R_e$ values for each of the plurality of first regeneration cocktails may be plotted on a bar diagram (e.g., $R_e$ values along the ordinate, first regeneration cocktails along the abscissa) so as to facilitate visual evaluation of the regeneration effect. In addition, during the step of sequentially contacting the biosensor surface with each of the plurality of first regeneration cocktails as set forth above (or with subsequent regeneration cocktails as set forth below), the biosensor surface may be contacted with an additional quantity of analyte to associate additional analyte with the surface-bound ligand. In particular, when the analyte level has decreased to about one third of its maximum level, the biosensor surface may be contacted with an additional quantity of analyte. It should also be understood that the analyte eluted from the biosensor surface may be collected for subsequent analysis (e.g., mass spectroscopy analysis).

In a further embodiment, the first regeneration cocktails having the two or three (or more) highest $R_e$ values are identified (e.g., from the aforementioned group of 18 first regeneration or screening cocktails identified in Table 1), and the two or three stock solutions that comprise these first regeneration cocktails are selected for further investigation and/or optimization.

Figure 2:
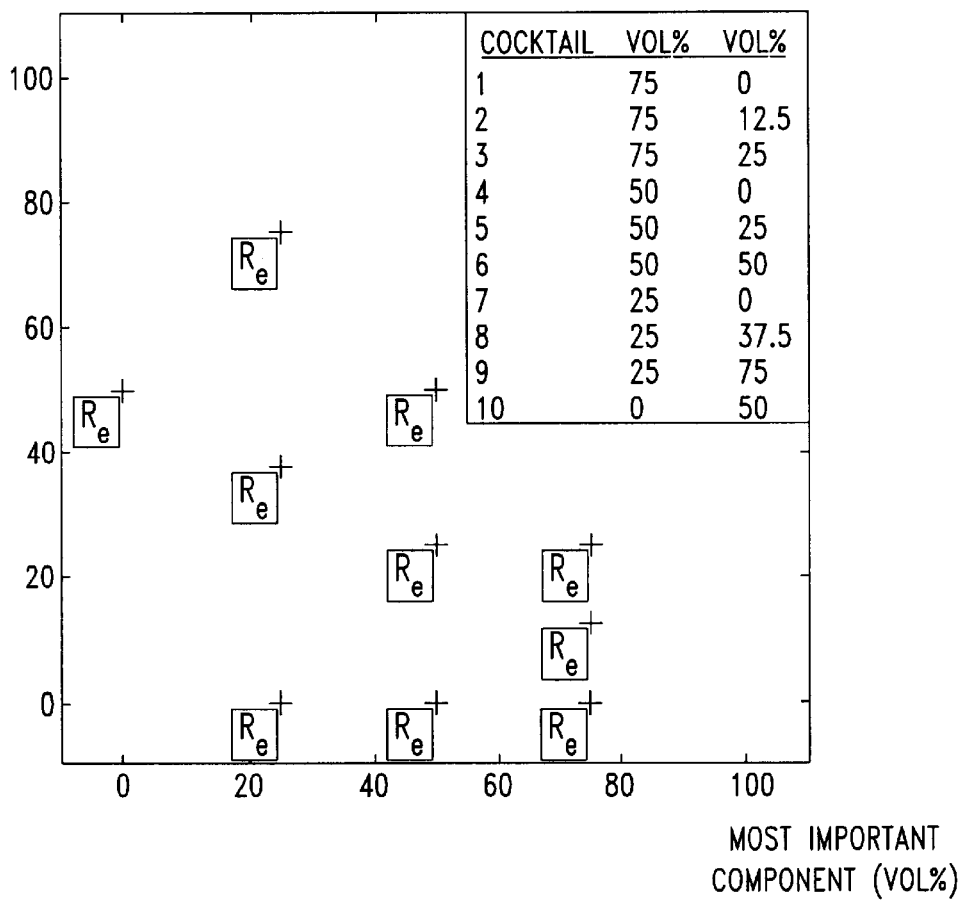
FIG. 2 shows a two-dimensional mixture optimization design ("MO2D"), wherein the compositions of 10 different two-stock cocktails are denoted.

Mixtures of these selected stock solutions, either with water or with other selected stock solutions, are referred to herein as "second regeneration cocktails." In order to generate a plurality of second regeneration cocktails, two different experimental designs may be employed to aid in determining possible two or three stock solution combinations for fuirther investigation. As illustrated in FIG. 2, a two-dimensional mixture optimization design ("MO2D") may be employed when two stock solutions have been selected; whereas, as illustrated in FIG. 3, a three-dimensional mixture optimization design ("MO3D") may be employed when three stock solutions have been selected.

Referring to FIG. 2, exemplary compositions for each of the two-stock second regeneration cocktails are denoted both in the table and on the design diagram. Specifically, the MO2D experimental design may, for example, result in 10 second regeneration cocktails of varying compositions. In addition, for those second regeneration cocktails in which the sum of volume percent of the two stock solutions is lower than 100%, water is added as a third solution. As exemplified, the calculated $R_e$ values for each of the 10 second regeneration cocktails may be plotted in the corresponding positions of the design diagram of FIG. 2, thereby facilitating visual interpretation of the experimental results.

Figure 3:
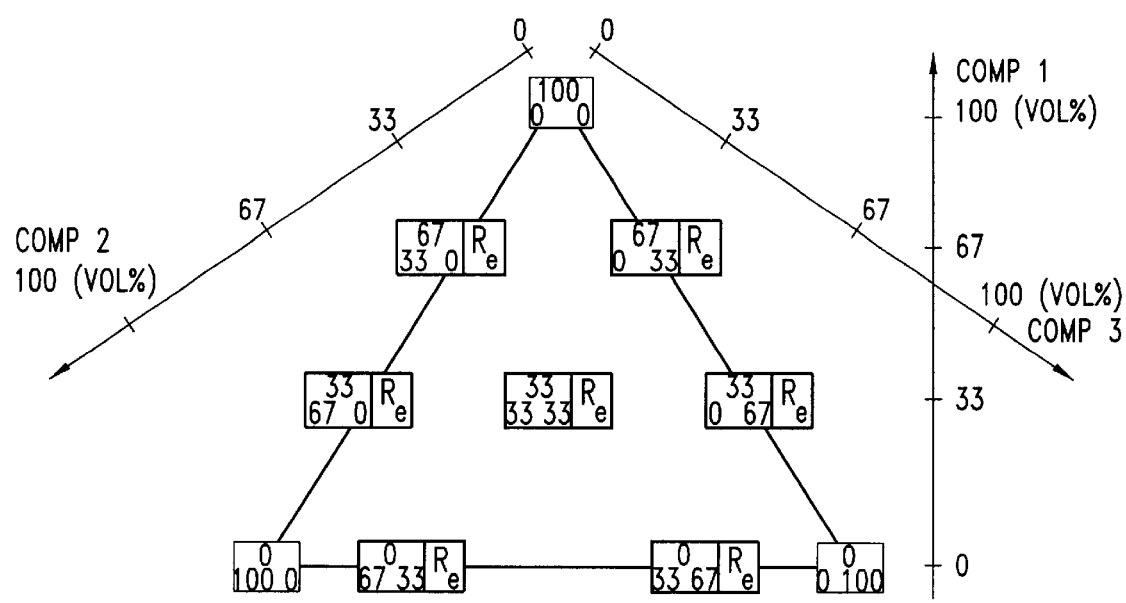
FIG. 3 shows a three-dimensional mixture optimization design ("MO3D"), wherein the compositions of seven different three-stock cocktails are denoted.

Similarly, referring to FIG. 3, the composition of each of the three-stock second regeneration cocktails are denoted on the design diagram. Specifically, the MO3D experimental design results, for example, in seven second regeneration cocktails of varying compositions. As exemplified, the calculated $R_e$ values for each of the seven second regeneration cocktails may be plotted in the corresponding positions of the design diagram of FIG. 3, thereby facilitating visual interpretation of the experimental results.

It should be understood, however, that the compositions of stock solutions and/or water as depicted in FIGS. 2 and 3 are exemplary of a representative embodiment of the present invention. Accordingly, compositions of stock solutions in ratios other than those depicted are possible for the second regeneration cocktails. For example, the second regeneration cocktails may comprise four (or more) different stock solutions.

In another aspect of the present invention, a plurality of second regeneration cocktails (such as those having compositions corresponding to either the MO2D or MO3D experimental designs discussed above) are sequentially contacted with the biosensor surface. As with the first regeneration cocktails, upon contacting the biosensor surface with each of the plurality of second regeneration cocktails, the regeneration effect for each of the second regeneration cocktails is measured as the percentage loss of analyte due to the cocktail injection. Based on these measurements, the second regeneration cocktails having the highest regeneration effect are identified. In general, the second regeneration cocktail with the highest $R_e$ value is sufficient for selection as the optimized regeneration solution.

Accordingly, in one embodiment, the method of this invention comprises the following steps:

(a) sequentially contacting the biosensor surface with each of a plurality of first regeneration cocktails, wherein each of said first regeneration cocktails is an aqueous solution comprising at least one acidic, basic, ionic, organic, detergent or chelating stock solution, and wherein at least one of said first regeneration cocktails comprises a mixture of at least two of said stock solutions;

(b) measuring the regeneration effect for each of said plurality of first regeneration cocktails to determine which of said plurality of first regeneration cocktails have the highest measured regeneration effect;

(c) selecting at least two different stock solutions present in said plurality of first regeneration cocktails having the highest measured regeneration effect;

(d) combining said at least two different stock solutions in various ratios to generate a plurality of second regeneration cocktails;

(e) sequentially contacting the biosenor surface with each of said plurality of second regeneration cocktails; and (f) determining the regeneration effect of each of said plurality of second regeneration cocktails and therefrom identifying a second regeneration cocktail as the optimized regeneration solution.

However, in those instances where the optimized regeneration solution has an unsatisfactory $R_e$ value (e.g., when the $R_e$ value is less than 90), additional iterations with a further (e.g., third) regeneration cocktails may be performed—that is, the ratio of stock solutions that comprise the second regeneration cocktails may be varied so as to generate a plurality of third regeneration cocktails. The third regeneration cocktails are then sequentially contacted with the biosensor surface and the regeneration effect for each of the cocktails is measured as before. In general, the third regeneration cocktail with the highest $R_e$ value may be selected as the optimized regeneration solution. The above steps may be repeated until the optimized regeneration solution is identified.

Thus, the method of this invention further comprises, after step (f) above, the following additional steps:

(g) combining said at least two different stock solutions in different ratios than step (d) to generate a plurality of third regeneration cocktails;

(h) sequentially contacting the biosensor surface with each of said plurality of third regeneration cocktails; and (i) determining the regeneration effect of each of said plurality of third regeneration cocktails and therefrom identifying a third regeneration cocktail as the optimized regeneration solution. The above steps may be repeated until the optimized regeneration solution is identified.

In another embodiment, the present invention is directed to a reagent kit comprising at least two different stock solutions selected from the library of six stock solutions; namely, a basic stock solution, an ionic stock solution, an organic stock solution, a detergent stock solution, and a chelating stock solution. The reagent kit may comprise at least three different stock solutions, four to five stock solutions, or six different stock solutions.

In yet another embodiment, the present invention is directed to a computer system (operatively connected to a device) for selecting an optimized regeneration solution for the regeneration of a biosensor surface having a surface-bound ligand and an analyte associated with the ligand. Specifically, the computer system has associated computer software and/or hardware capable of performing the following steps:

(a) instructing a device to combine a series of stock solutions in various ratios to generate a plurality of first regeneration cocktails;

(b) sequentially controlling the device to contact the biosensor surface with each of said plurality of first regeneration cocktails;

(c) determining the regeneration effect of each of said first regeneration cocktails on the biosensor surface based on measurements received from the device;

(d) selecting at least two different stock solutions having the highest regeneration effect;

(e) instructing the device to combine a subset of said at least two different stock solutions in varying ratios to generate a plurality of second regeneration cocktails;

(f) sequentially controlling the device to contact the biosenor surface with each of said second regeneration cocktails; and (g) determining the regeneration effect of each of said second regeneration cocktails based on measurements received from the device, and therefrom identifying a second regeneration cocktail as the optimized regeneration solution.

In a further aspect of this embodiment, the method further comprises, after step (g), the following additional steps:

(h) instructing the device to combine the subset of said at least two different stock solutions in different ratios than step (e) to generate a plurality of third regeneration cocktails;

(i) sequentially controlling the device to contact the biosensor surface with each of said third regeneration cocktails; and (j) determining the regeneration effect of each of said third regeneration cocktails based on measurements received from the device, and therefrom identifying a third regeneration cocktail as the optimized regeneration solution.

Figure 4A:
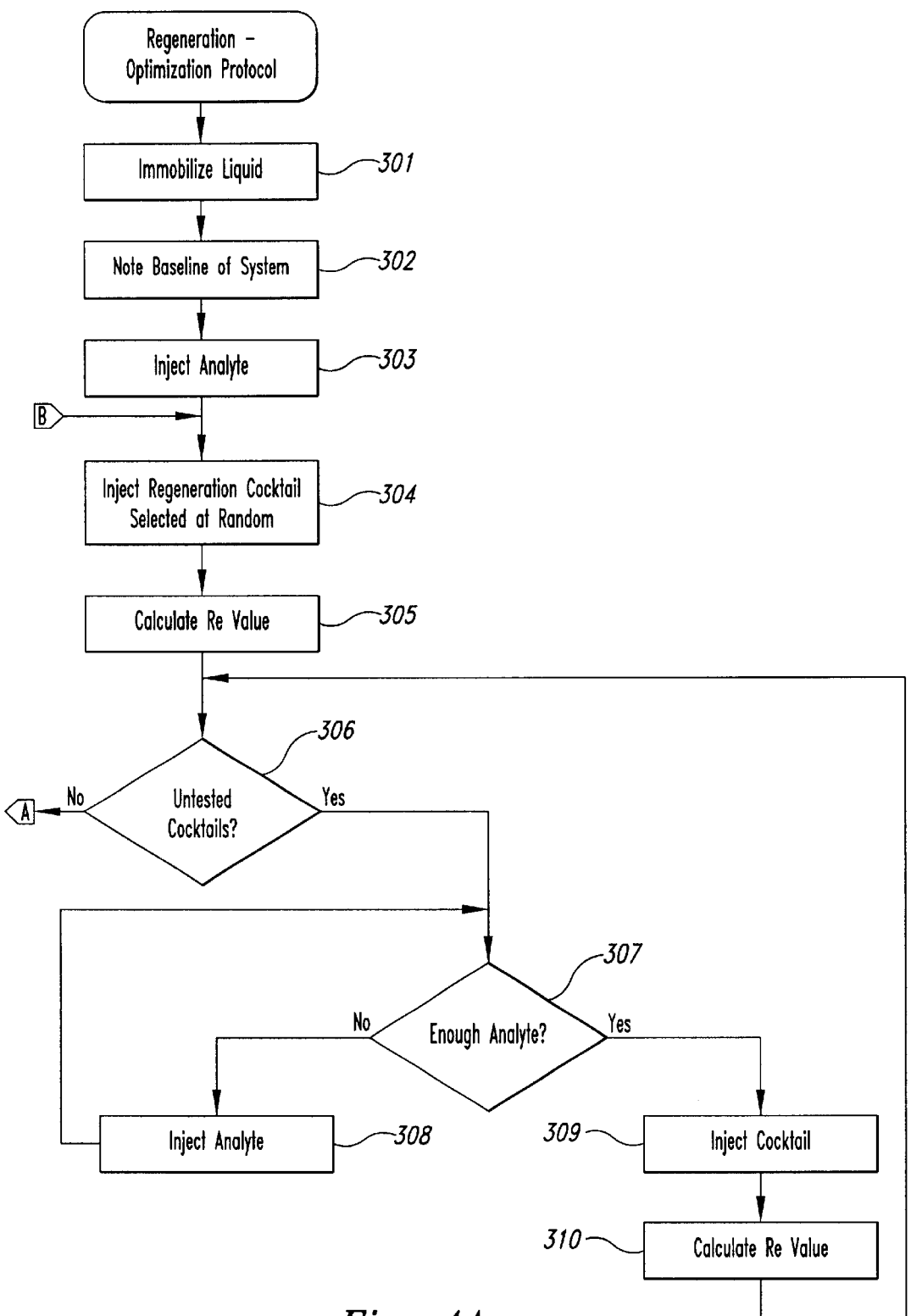
FIG. 4A and FIG. 4B provide a flowchart illustrating the steps for identifying and optimizing the regeneration conditions for a biosensor surface.
Figure 4B:
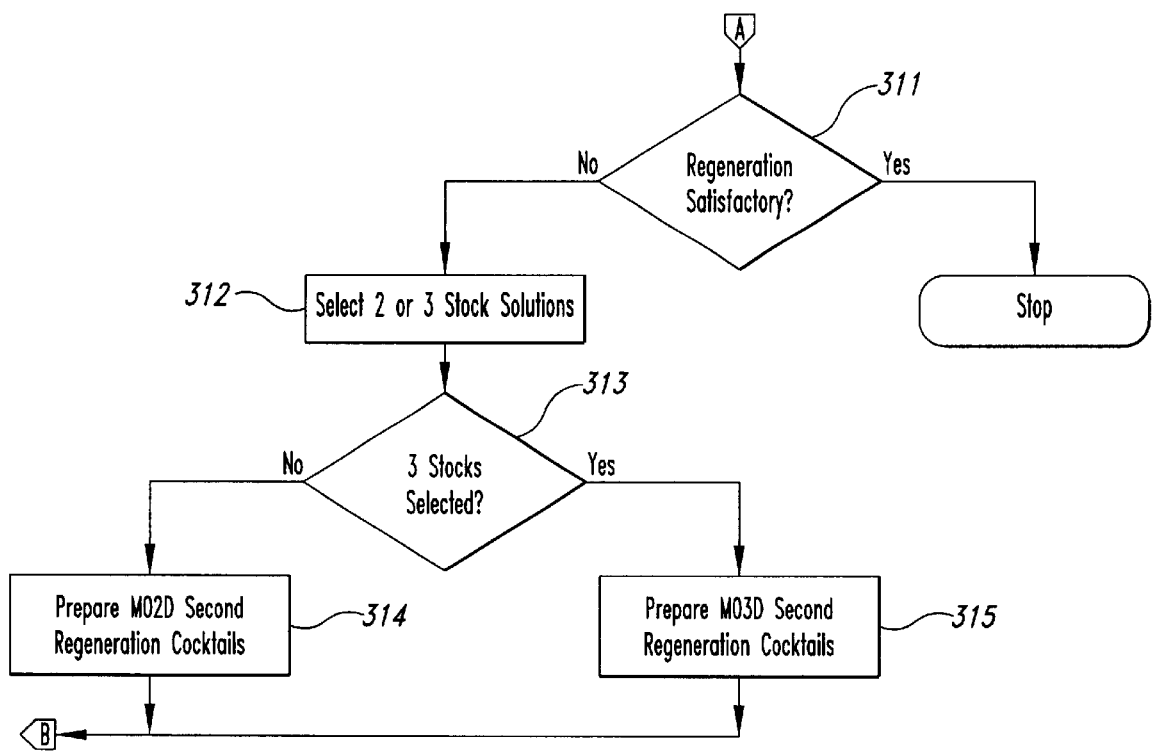

In yet another aspect of this embodiment, the computer system substantially automates the routine illustrated in FIGS. 4A and 4B. Specifically, FIGS. 4A and 4B provide a flowchart illustrating the steps for identifying and optimizing the regeneration conditions for a biosensor surface of, for example, a BIAcore instrument. Referring to FIG. 4A, an appropriate ligand (i.e., selected from a ligand and analyte interaction pair under investigation) is immobilized onto the biosensor surface in step 301. In general, there should be enough immobilized ligand so as to obtain 300–1000 RU maximal binding capacity. Following the ligand immobilization, a plurality of first regeneration cocktails are made (not shown) from the previously disclosed library of six stock solutions, wherein at least one of the first regeneration cocktails comprises a mixture of at least two different stock solutions. While maintaining the running buffer, the baseline of the system is noted in step 302. Next, analyte is injected into the running buffer for a selected period of time (step 303) in order to associate the analyte with the immobilized ligand. One of the previously prepared regeneration cocktails is selected (e.g., randomly) and injected over a 30 second period into the running buffer in step 304. The regeneration effect ($R_e$) value for the selected regeneration cocktail is then calculated in step 305.

The regeneration-optimization protocol then decides whether there are any other regeneration cocktails available for further analysis (step 306). If there are additional regeneration cocktails available, the regeneration-optimization protocol determines whether there is a sufficient about of analyte still associated with the immobilized ligand (step 307). In general, when the analyte level has decreased to about one third of its maximum level, the biosensor surface should be contacted with additional analyte. Accordingly, if there is not enough analyte, additional analyte is injected into the running buffer in step 308. On the other hand, if there is enough analyte associated with the immobilized ligand, then one of the remaining regeneration cocktails is selected (e.g., randomly) and injected into the running buffer as before (step 309). The regeneration effect ($R_e$) value for the selected regeneration cocktail is then calculated in step 310. The regeneration-optimization protocol then decides whether there are still any other regeneration cocktails available for further analysis (i.e., "loops-back" to step 306).

If there are not any additional regeneration cocktails available for further analysis (see FIG. 4B), then the regeneration-optimization protocol determines whether any of the analyzed regeneration cocktails provides a satisfactory regeneration of the biosensor surface (step 311). In general, a satisfactory regeneration of the biosensor surface is achieved when the regeneration effect ($R_e$) is greater than 99% for any of the analyzed regeneration cocktails. If the analyzed regeneration cocktails are not satisfactory, then the regeneration-optimization protocol selects the two or three stocks solutions (step 312) from the two or three first regeneration cocktails having the highest regeneration effect ($R_e$) values for further investigation and/or optimization (i.e., for further formulation into second regeneration cocktails).

The regeneration-optimization protocol then determines whether three stock solutions have been selected for further investigation and/or optimization (step 313). If three stock solutions have not been selected, that necessarily means that only two stock solutions have been selected. Accordingly, in step 314 a plurality of second regeneration cocktails are prepared in accordance with the compositions of the previously disclosed two-dimensional mixture optimization design ("MO2D"). As before, one of these second regeneration cocktails is selected (e.g., randomly) and injected over a 30 second period into the running buffer in step 304 (i.e., "loops-back" to step 304), and the subsequent steps of the regeneration-optimization protocol are repeated. If, on the other hand, three stock solutions have been selected, then a plurality of second regeneration cocktails are prepared in step 315 in accordance with the compositions of the previously disclosed three-dimensional mixture optimization design ("MO3D"). Again, one of these second regeneration cocktails is selected (e.g., randomly) and injected over a 30 second period into the running buffer in step 304 (i.e., "loops-back" to step 304), and the subsequent steps of the regeneration-optimization protocol are repeated.

The above-identified regeneration-optimization protocol will usually result in regeneration cocktail that provides satisfactory regeneration of the biosensor surface (i.e., regeneration effect ($R_e$) value that is greater than 99%). If, however, no satisfactory regeneration is achieved, then other combinations and/or different ratios of the stock solutions may be tested. In addition, the pH of the stock solutions may also be adjusted, and the cocktails may be injected into the running buffer in several short pulses as opposed to a constant flow. Moreover, for those regeneration cocktails that have substantially different compositions than those of the predefined mixing ratios as set forth above (e.g., a combination of four stock solutions), or if the cocktail composition has significantly deviated from those previously tested, a check for precipitation should be performed by refrigerating the cocktail for at least one hour. The precipitation check may avoid injections of particles that can clog the microfluidic cartridge of, for example, the BIAcore instrument.

In yet a further embodiment, the present invention is directed to a computer-readable medium containing the instructions for performing the above-identified steps for selecting an optimized regeneration solution for the regeneration of a biosensor surface having a surface-bound ligand and an analyte associated with the ligand.

The above disclosure has primarily focused on the selection of an optimized regeneration solution for regenerating a biosensor surface having a surface-bound ligand and analyte associated therewith. In a related embodiment of this invention, measuring the analyte-ligand binding interaction during association, steady state, and dissociation conditions (including regeneration) with the various above-identified stock solutions (including diluted forms thereof) is performed to provide information concerning the potential activity or functionality of the ligand and/or analyte. More specifically, by determining the kinetic parameters related with the association and dissociation of the analyte-ligand binding pair (as well as analogues as thereof) in several different characterization solutions or running buffers of the present invention, structure-activity relationships (SARs) of the ligand and/or analyte may be predicted. Such information is referred to herein as a "characteristic" of the ligand and/or analyte, while the process for determining the same is referred to as "characterization." In addition, as used herein, the term "characterization solution" encompasses the above-identified stock solutions and regeneration cocktails made therefrom, as well as more dilute solutions thereof. As such, the term "characterization solution" is to be construed broadly so as to covers a full spectrum of possible solution concentrations (e.g., 1 pM aqueous solution to saturation).

As noted above, characterization of the ligand and/or analyte of the ligand-analyte pair has tremendous value, particularly in the context of predicting SAR. In the practice of this invention, this may be accomplished by contacting a biosensor surface (having a surface-bound ligand) with a plurality of characterization solutions of this invention and, while the characterization solution is in contact with the biosensor surface, introducing an analyte of interest into the characterization solution (e.g., running buffer) for a selected period of time, measuring the biospecific interaction effect (e.g., association rate, analyte surface concentration at steady state, dissociation rate and/or regeneration effect) for each of said plurality of characterization solutions, and therefrom characterizing the ligand and/or analyte. Such characterization may then be compared with similar characterizations made for one or more test molecules, thereby allowing one to predict the SAR of the ligand and/or analyte of interest. For example, a mathematical model may be used that, given the analyte or ligand structure, predicts the analyte or ligand activity. In addition, the properties of the mathematical model may be used for characterization and communication of the biospecific interaction effect of the analyte or ligand.

Accordingly, in another aspect of this invention, a method for characterizing a ligand and/or analyte associated with a biosensor surface is disclosed, wherein the method comprises the following steps:

(a) sequentially contacting the biosensor surface having a surface-bound ligand with each of a plurality of characterization solutions;

(b) introducing the analyte into each of said plurality of characterization solutions so as to interact the analyte with the surface-bound ligand;

(c) measuring at least one of the association rate, surface-bound analyte concentration, dissociation rate, and regeneration effect of the analyte-ligand interaction for each of said plurality of characterization solutions; and (d) characterizing the ligand and/or analyte associated with the biosensor surface based on at least one of the association rate, surface-bound analyte concentration, and dissociation rate of the analyte-ligand interaction for each of said plurality of characterization solutions.

In a further aspect of this embodiment, the method further comprises, after step (d), the following additional step:

(e) comparing the characterization of the ligand and/or analyte associated with the biosensor surface with a set of predetermined characterizations of other test molecules and thereby predicting the activity of the ligand and/or analyte associated with the biosensor surface.

It should be understood that, as used herein, the term "biospecific interaction effect" encompasses not only the aforementioned dissociation kinetic parameters, but also includes association kinetic parameters as well as the steady state aspects of the binding interaction between the ligand and analyte of interest (e.g., affinity). Thus, as used in the context of this invention, biospecific interaction effect includes association rate, analyte surface concentration at steady state, dissociation rate, and regeneration effect, all of which may be measured with respect to each of the characterization solutions. The measured biospecific interaction effect may then be compared with a set of predetermined characterizations of other test molecules so as to provide valuable information concerning the potential activity or functionality of the ligand and/or analyte.

Figure 11:
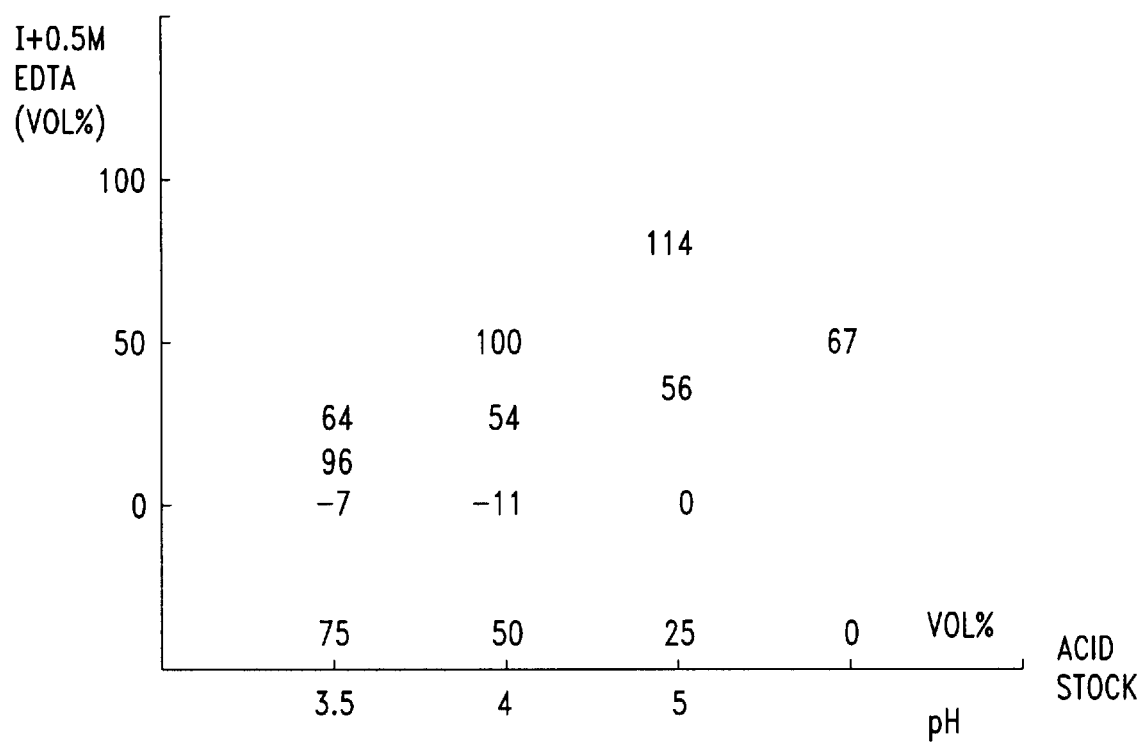
FIG. 11 illustrates the measured $R_e$ values for a two-dimensional mixture optimization design ("MO2D") experiment on a GST/polyclonal antiGST system, wherein the regeneration cocktails include combinations of acidic (A) and ionic (I) stock solutions, and wherein the volume percent and acidity of the acidic (A) stock were varied and the ionic (I) stock included 0.5M EDTA.

For example, a representative set of predetermined regeneration characterizations of test molecules (i.e., ligand-analyte binding pairs) is illustrated in FIG. 11, and further discussed in the Example below. Referring to FIG. 11, a series of ten monoclonal antibodies were each characterized against the 18 regeneration cocktails of Table 1 above. Assuming, for example, that the identify of one of the MAbs was not known, such as the MAb g2b__clone2, comparing the characteristics of that antibody with the characteristics of the remaining nine MAb, one can readily predict that the activity of g2b__clone2 would be most similar to that of g2a__clone3 and g2b__clone3. Accordingly, by characterizing a number of test molecules, SAR may be predicted by comparison of the sample molecule's characteristics with those of the predetermined test molecules.

Similarly, characterizations of analyte-ligand complexes may be performed by determining the kinetic (i.e., association and dissociation) parameters of the interaction pair in a plurality of diverse buffers (i.e., characterization solutions), preferably at two or more temperatures. The complete binding cycle (i.e., both association and dissociation) for the analyte-ligand interaction pair is performed in each of the plurality of buffers, and kinetic constants may be calculated for each buffer. The plurality of buffers or characterization solutions may, for example, be selected from the above-identified stock solutions, the regeneration cocktails of Table 1 and/or Table 2, as well as diluted forms thereof. In addition, any one of these solutions may be varied by having other additives, including acids, bases, salts, organic solvents, and/or detergents. In general, for purposes of analysis, the plurality of diverse buffers may be selected according to the experimental design rules disclosed above.

In addition to theses analyte-ligand characterizations, several analogues of the analyte and/or ligand may also be selected for characterization. That is, a plurality of analogues of the characterized analyte and/or ligand may be selected for subsequent characterizations, wherein the kinetic parameters of the analogue binding interactions are measured in each of the previously selected characterization solutions. For those analyte-ligand interaction pairs that have suitable analogues, a mathematical model may be employed to connect the measured kinetic constants with a structural description of the molecules of interest (e.g., peptides, small molecules, proteins, and RNA/DNA), thereby allowing one to predict the SAR of other analogues. The properties of the mathematical model may be used to describe and communicate functional information in, for example, functional databases. Moreover, a collection of such characterizations of known analyte-ligand interaction pairs and analogues thereof, has tremendous value in that they enable researchers to more accurately predict the activity and/or functionality of other closely related molecules. As used herein, the term "analogue" with respect to an analyte means a molecule capable of specifically binding to the ligand of the analyte-ligand interaction pair in the same or similar fashion as the analyte, whereas the term "analogue" with respect to a ligand means a molecule capable of specifically binding to the analyte of the analyte-ligand interaction pair in the same or similar fashion as the ligand.

Furthermore, the above-identified method for characterizing a ligand and/or analyte associated with a biosensor surface also finds utility in quantitative assays, and multi-buffer epitope mapping. For example, in developing quantitative assays for determination of vitamin concentration in food stuff, researchers are often interested in knowing how sensitive a specific reagant, typically a MAb, is to variations in its chemical environment. By using the characterization methods of this invention, researchers are able to choose the specific reagant that is least affected by changes in the chemical environment and by inhomogenous buffers (e.g., by monitoring how stable reagants for a quantitative assay behave with respect to inhomogenous sample matrices).

Accordingly, a researcher may, for example, set up an inhibition assay for determination of biotin concentration in infant formulas, and prepare artificial samples to which a known quantity of biotin has been added. The artificial samples are preferably diverse (e.g., having various salt concentrations, pH, fiber content, etc.). In this exemplary situation, the measured concentration of biotin in the artificial samples will deviate from the known concentration. By subsequently characterizing several different reagants (e.g., at least three or four MAbs), a researcher may formulate a predictive model by determining biotin concentrations in several different infant formulas using all the reagants that were characterized. For example, those MAbs that give large deviations in the real samples may also give large deviations in the artificial samples, thereby allowing a predictive mathematical correlation to be expressed. Other substances that may be of interest for purposes of accurate concentration determinations include (but are not limited to) drug residues, hormones and toxins.

Similarly, researchers often desire to verify that manufactured proteins have their expected structures and are not point mutated. Accordingly, a researcher may, for example, immobilize on a biosensor surface three or four different MAbs directed to different epitopes on the same protein. The binding interactions between the protein and three or four different MAbs may then be characterized by employing the characterization solutions and methodologies of this invention (e.g., injecting the protein into several characterization solutions so as to interact with the surface-bound MAbs). In addition, similar protein analogues (e.g., point mutated proteins) may further be characterized under the same conditions. A collection of such characterization data will serve as a unique "fingerprint" that reveal small protein changes, even if they are outside all MAb epitopes.

For purposes of illustration and not limitation, the following example more specifically discloses various aspects of the present invention are provided

EXAMPLE

This example illustrates a representative method of the present invention for identifying an optimized regeneration solution in connection with four different ligand-analtye (i.e., antibody-antigen) systems.

Materials and Methods

Stock Solutions

Six stock solutions, designated acidic (A), basic (B), ionic (I), organic (O), detergent (D) and chelating (C), were formed by combining the components listed in Table 3.

TABLE 4

| Acidic | Basic | Ionic | Organic | Detergent | Chelating |
|---|---|---|---|---|---|
| oxalic | ethanol-amine | KSCN | DMSO | CHAPS | EDTA |
| phosphoric | Na3PO4 | MgC12 | formamide | zwittergent | |
| formic | piperazine | urea | ethanol | tween 80 | |
| malonic | glycine | guanidine | acetonitrile | tween 20 | |
| | | | 1-butanol | triton X-100 | |

Table Legend:

A: Equal volumes of oxalic acid, $H_3PO_4$, formic acid and malonic acid, each in 0.15M, mixed and adjusted to pH 5.0 with NaOH.

B: Equal volumes of ethanoleamine, $Na_3PO_4$, piperazin and glycine, each in 0.20M, mixed and adjusted to pH 9.0 with HCl.

I: A solution of KSCN (0.46M), $MgCl_2$ (1.83M), urea (0.92M), guanidinHCl (1.83M).

O: Equal volumes of DMSO, formamide, ethanol, acetonitrile and 1-butanol.

D: A solution of 0.3% (weight/weight) CHAPS, 0.3% (w/w) zwittergent 3–12, 0.3% (volume/volume) tween 80, 0.3% (v/v) tween 20 and 0.3% (v/v) triton X-100.

C: A 20 mM EDTA solution.

First Regeneration Cocktails

Eighteen first regeneration cocktails were prepared as disclosed in Table 5. With regard to the first generation cocktails, equal volumes of the six stock solutions (designated A, B, I, O, D and C) and water were mixed in the proportions noted. For example, the first regeneration cocktail "Aww" was a mixture of one volume stock solution A and two volumes water, whereas "BAw" contained one volume each of stock solution B, stock solution A and water.

TABLE 5

| Aww | Bww | Iww | Oww | Dww | Cww |
| BAw | BDw | BCw | AIw | AUw | ADw |
| ACw | Idw | ICw | DOw | DCw | OCw |

Ligands, Analytes and Coupling to Sensor Chip

Ligand polyclonal anti-GST Ab and analyte GST; ligands anti-p24 MAbs 609 and 576 and analyte p24; and ligand protein A and analytes MAbs g3_clone2, g2b_clone3, g2b_clone2, g2a_a clone3, gla, g3_clone3, anti-theofyllin MAb 459, and anti-p24 MAb 609 were obtained from Biacore AB (Uppsala, Sweden). The protein A analytes anti-clenbuterol polyclonal Abs r200 and r154 were a gift from Dr. Chris Elliot (Belfast, Ireland).

CM5-chips, HBS running buffer and an Amine coupling kit (for use with the BIAcore instrument) were also obtained from Biacore AB. The ligands were coupled to CM-5 chips in BIACORE 1000 according to Jönsson et al (Jönsson et al., *BioTechniques* 11:620–27, 1991). The CM-5 surface was activated with a 7 minutes EDC/NHS pulse. The ligands, solved in 10 mM acetate buffer pH 5.0, were then injected for 3–5 minutes. Next a 3.5 minutes pulse of 1.0 M ethanoleamine pH 8.5 deactivated the surface. The immobilization level for the ligands were typically about 4000 RU.

Run and Evaluation

BIACORE 1000 was programmed to test the regeneration effect of the 18 different first regeneration cocktails at two different cycles. First a 10 minute analyte injection (flow 2 $\mu$l/min) was performed. The original baseline and the obtained analyte level were saved. Then, 30 second injections (flow 20 $\mu$l/min) of the different cocktails were performed until the analyte level had decreased to 30% of the original value. When low analyte level was detected, a new analyte injection was performed, followed by more cocktail injections. The cocktails were injected in random order. BIACORE 1000 was equipped with a computer system having software with if-then capabilities which made possible a complete automation of the experiments. However, the experiments could as well have been performed in manual mode as described below.

A regeneration effect value ($R_e$) was assigned for each of 18 first regeneration cocktails (i.e., screening cocktails). This $R_e$ value was calculated as the percentage loss of analyte due to the cocktail injection. Thus, with the initial baseline response level as reference, RU values of analyte loss and analyte level were calculated for each screening cocktail. In order to correct for dissociation of the ligand-analyte complex, the sensorgram before the screening cocktail injection was extrapolated to be comparable with the response level after the screening cocktail injection.

Figure 5:
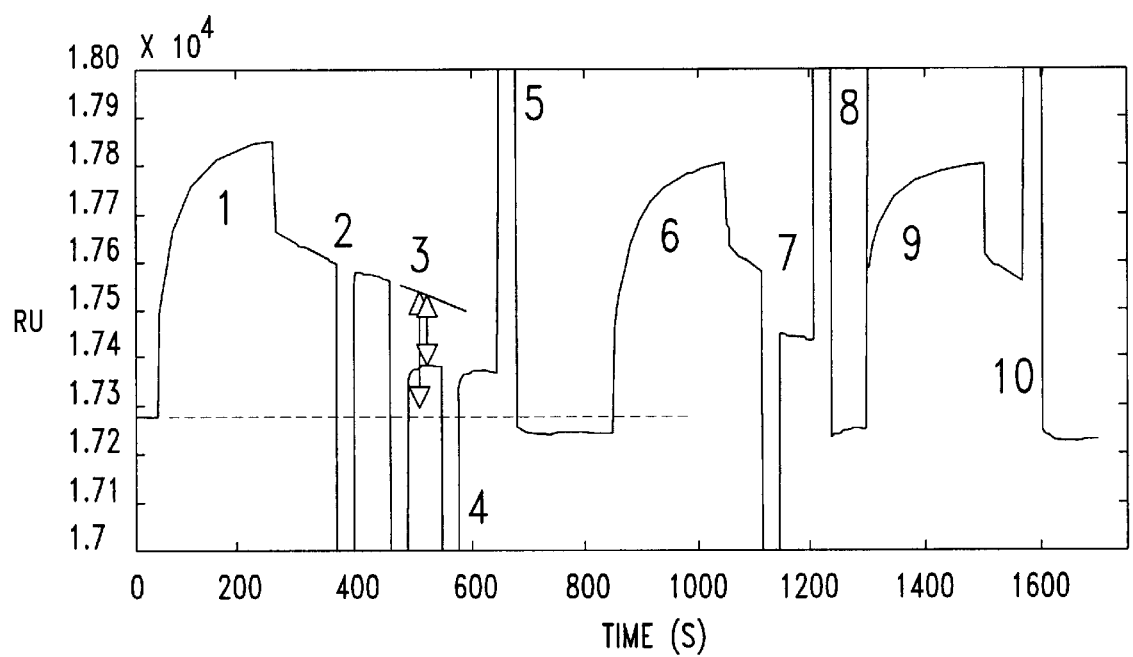
FIG. 5 shows a sensorgram from a regeneration-optimization protocol run with a p24/MAb 609 system.

More specifically, FIG. 5 shows a sensorgram from a regeneration-optimization protocol run with the MAb 609-p24 system. Three analyte injections and seven cocktail injections are shown. The injections were performed in the following order: analyte p24, Cww, ADw, Bww, ICw, analyte p24, Aww, ODw, analyte p24 and AIw (numbered 1–10, respectively). For injection 3 (ADw) the extraction of analyte level (long arrow) and analyte loss (short arrow) are shown. The baseline decreased significantly during the first cocktail injections which is indicated by the extended original baseline. The peak in the beginning of injection 9 (analyte p24) was due to insufficient cleaning after injection 8 (ODw). Execution of an extraclean after injection 8 would provide sufficient cleaning of the microfluidic system.

Screening and Evaluation

The regeneration effect of the 18 different first regeneration cocktails were tested as described above. The results were evaluiated visually by plotting a bar diagram that illustrated the measured $R_e$ value for each screening cocktail. The stock solutions with the highest $R_e$ values were chosen for further optimization.

In the second step, the two or three stocks with largest contribution to high $R_e$ values were further investigated. Two different experimental designs for optimization were used. When two stocks were chosen for optimization, a two-dimensional mixture optimization design ("MO2D") was used. This design is illustrated in FIG. 2, wherein the composition of the cocktails are denoted both in the table and the diagram. For those cocktails where the sum of volume percent was lower than 100%, water was added as a third solution. The evaluation of a two-stock optimization was visual. As exemplified in FIG. 2, the calculated $R_e$ values may be plotted in the corresponding positions in the design diagram.

When an optimization with three stocks was performed, a three-dimensional mixture optimization design ("MO3D") was used. Seven cocktails, as illustrated in FIG. 3, were mixed, tested and assigned $R_e$ values. The composition of the cocktails are denoted in the left hand boxes in the diagram. The evaluation of the three-stock optimization was also visual. As exemplified in FIG. 3, the calculated $R_e$ values may be plotted in the corresponding positions in the design diagram.

Results

The screening cocktails were designed to include diluted single stocks and all two part combinations of stocks. Of the 21 possible screening cocktails three had to be excluded: BIw and BOw formed precipitate, whereas scouting experiments showed that IO was too aggressive. That is, after an injection of an IO regeneration cocktail the maximal binding capacity was decreased and the baseline was increased significantly. Consequently, due to the necessity of gentle screening solutions, IO was excluded.

The RO protocol of the present invention was used to identify an optimized regeneration solution for four specific ligand-analyte systems: (1) p24/MAb 609 system; (2) p24/MAb 576 system; (3) GST/polyclonal anti-GST system and (4) SpA/MAbs.

Figure 6:
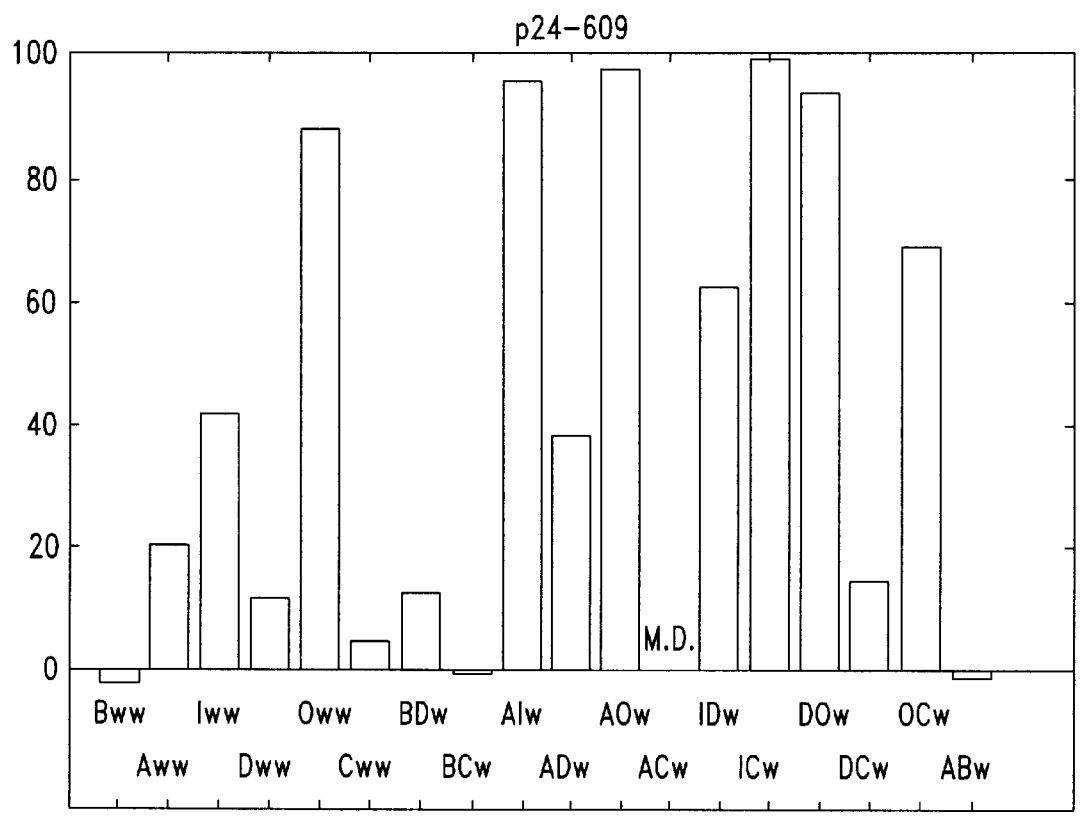
FIG. 6 illustrates the measured $R_e$ values for a plurality of screening cocktails tested on a p24/MAb 609 system.
Figure 7:
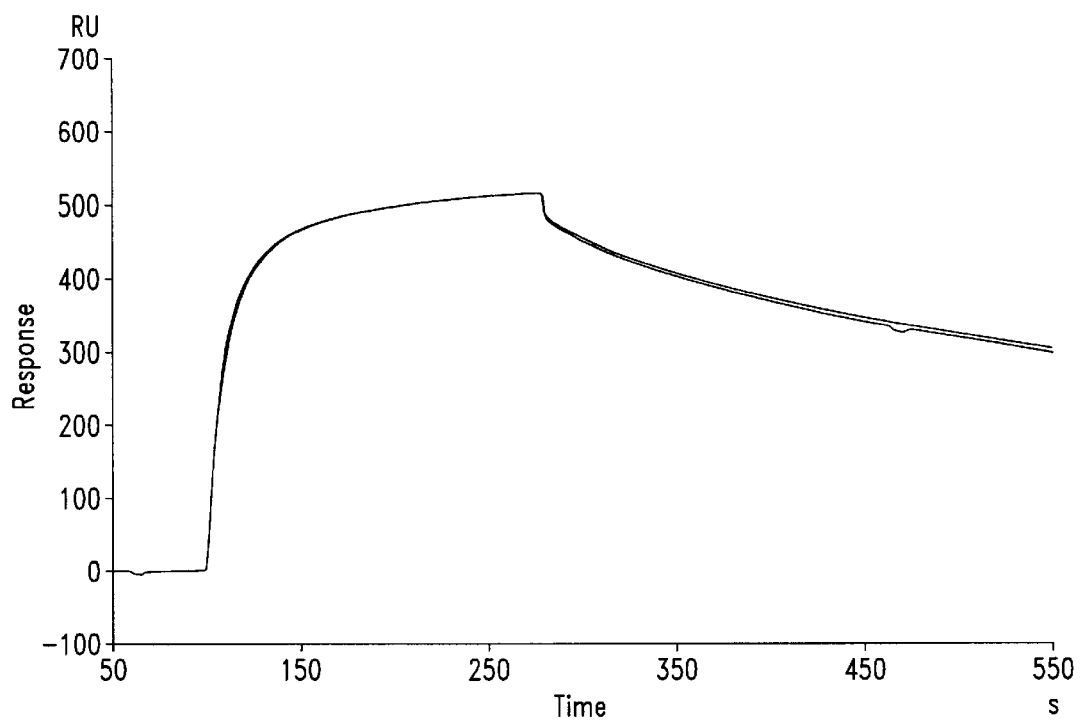
FIG. 7 shows a sensorgram having an overlay plot of the regeneration of a p24/MAb 609 system with an AIC regeneration cocktail, wherein the first plot represents the first regeneration and the second plot represents the twentieth regeneration.

(1) For the p24 MAb 609 system, several of the screening cocktails were identified as possible regeneration agents. The cocktail ICw seemed to offer complete regeneration in 30 seconds. AIw, AOw and DOw also gave high $R_e$ in the screening session. Cocktails containing stock O caused an unstable baseline for approximately 30 seconds. The $R_e$ measured for each screening cocktail is plotted in FIG. 6. Control experiments showed that ICw only regenerated the surface close to completely. Thus, the cocktail AIC was successfully tested as regeneration agent for the p24-MAb609 system. In the control experiment, the MAb surface was regenerated 20 times with AIC. In FIG. 7, an overlay plot of cycle 1 and cycle 20 is shown. The plot clearly shows that the surface did withstand repeated injections of the cocktail AIC. (The p24-MAb609 system has been traditionally regenerated with 100 mM HCl.)

Figure 8:
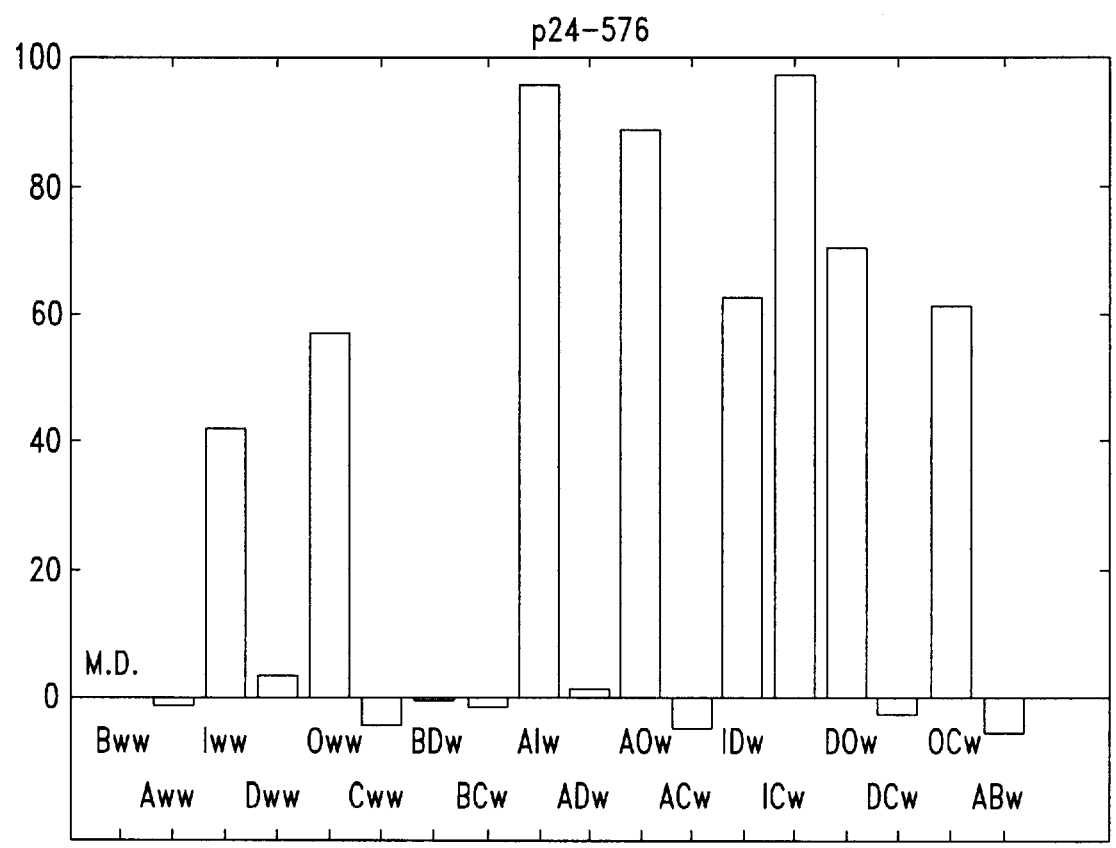
FIG. 8 illustrates the measured $R_e$ values for a plurality of screening cocktails tested on a p24/MAb 576 system.
Figure 9:
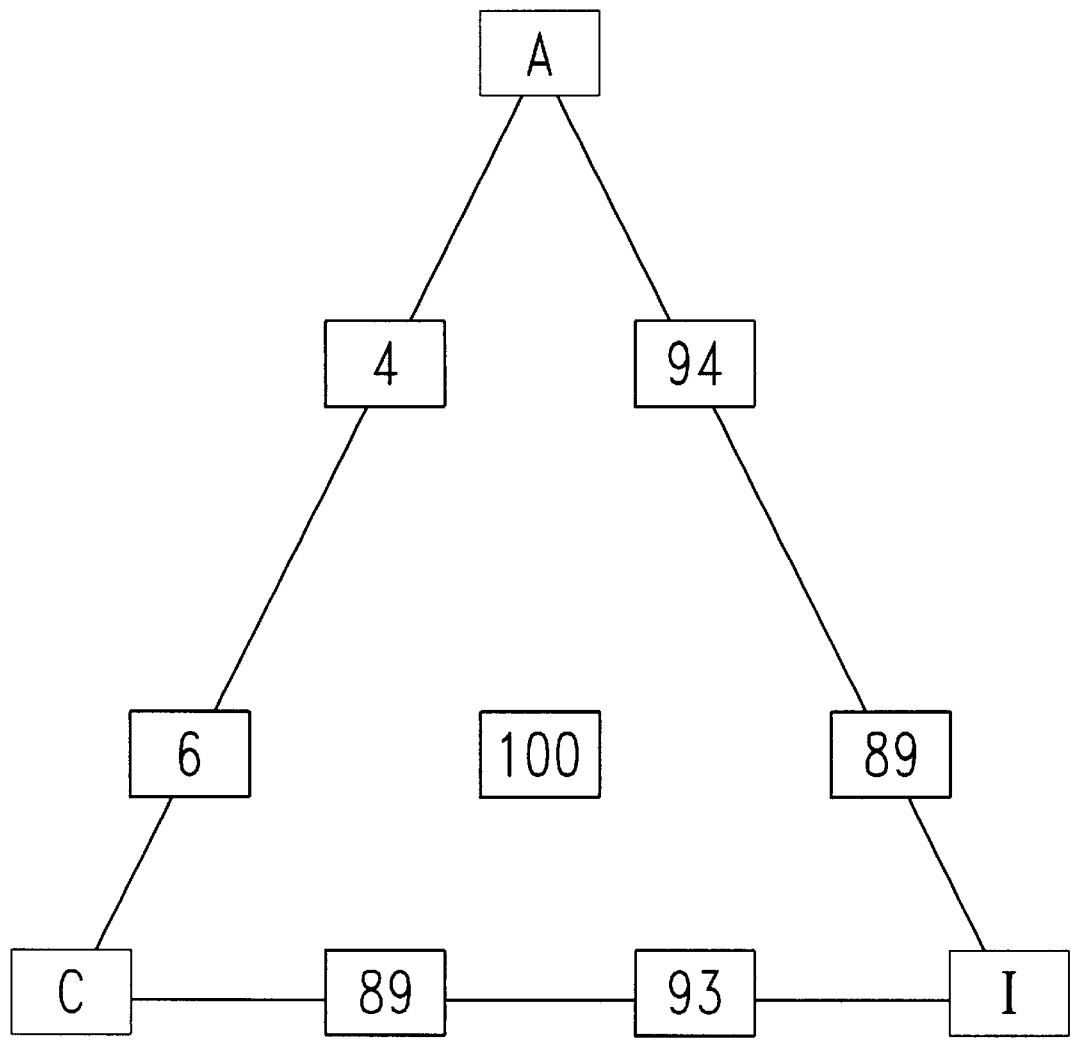
FIG. 9 illustrates the measured $R_e$ values for a three-dimensional mixture optimization design ("MO3D") experiment on a 24/MAb 576 system, wherein the regeneration cocktails include combinations of acidic (A), ionic (I), and chelating (C) stock solutions.

(2) For the p24 MAb 576 system, ICw was also the best screening cocktail (ICw had a $R_e$>90). The $R_e$ measured for each screening cocktail is plotted in FIG. 8. Based on these results, an optimization with the stocks A, I and C was performed. In this experiment, a regeneration cocktail which offered complete regeneration was identified. The cocktail AIC had $R_e \approx 100$ and was therefore identified as a suitable regeneration agent. The optimization results also indicated that all three components are needed to obtain complete regeneration, although the stock I contributes most to the regeneration properties of the cocktails. The results are shown in FIG. 9. (The p24-MAb576 system is normally regenerated with 1M ethanolamine pH 10.4.)

Figure 10:
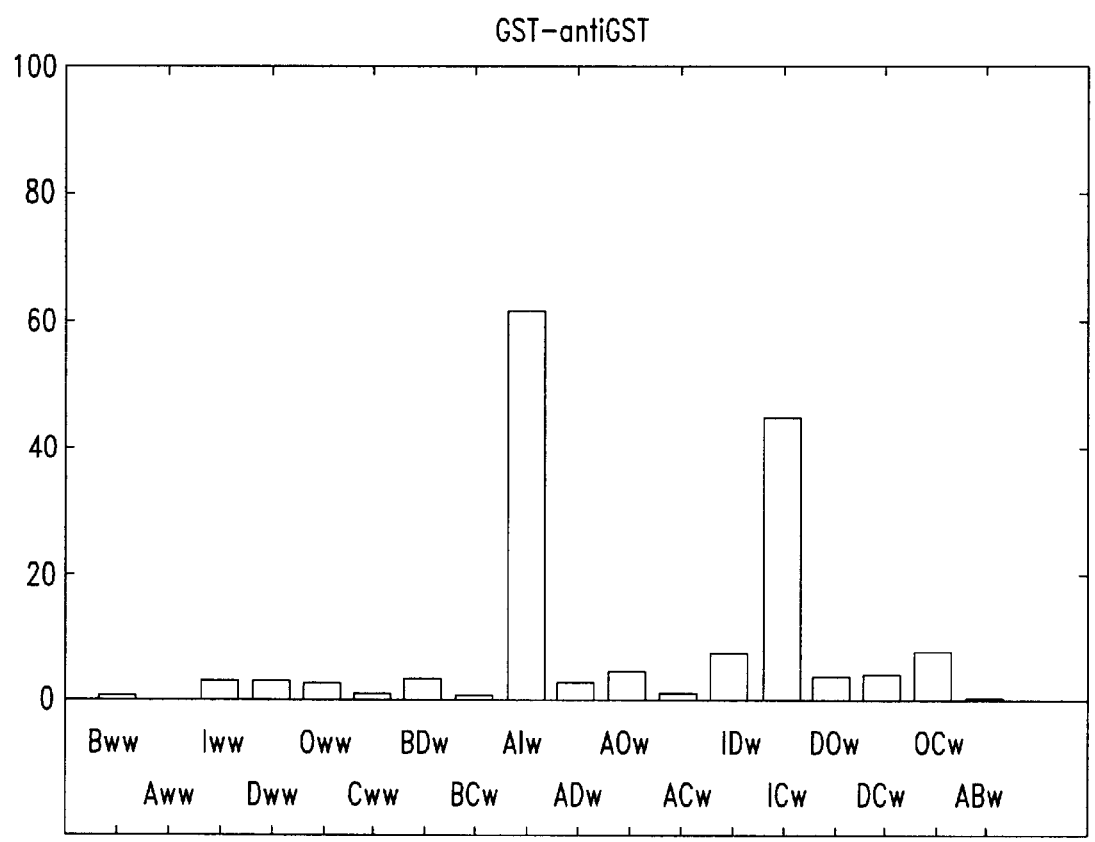
FIG. 10 illustrates the measured $R_e$ values for a plurality of screening cocktails tested on a GST-polyclonal antiGST system.

(3) The regeneration effects for the screening cocktails for the GST- polyclonal antiGST system are plotted in FIG. 10. The most successful cocktails, AIw and ICw had $R_e$ values of approximately 60 and 45 respectively. Two stock solutions were chosen for optimization. A was chosen as the best stock solution and the mix I +(0.5M EDTA) (10+1) as second best. An optimization using the MO2D design was performed. In this design, not only was the volume percent of the acid stock solution varied, the pH of the stock was decreased with increasing volume percent as well. The results are plotted in FIG. 11 (based on the MO2D format of FIG. 2). Visual evaluation of the result plot show that one volume A with pH adjusted to 4 mixed with one volume I+(0.5M EDTA) (10+1) regenerated the surface completely. (The GST-antiGST is normally regenerated with a 10 mM glycine solution pH 2.20.)

(4) In addition, to illustrate both the regeneration and characterization aspects of this invention, the RO protocol was applied to a fourth system—that is, SpA, as the ligand, with ten different MAb analytes: (a) g3_clone2, (b) g3_clone3, (c) g2b_clone2, (d) g2b_clone3, (e) g2a, (f) g1a, (g) anti-theofyllin MAb 459, (h) anti-p24 MAb 609, (i) polyclonal anti-clenbuterol Abs r200 and (j) r154. The resulting $R_e$ values are plotted in FIG. 12.

With regard to regeneration optimization, ICw and AIw had high regeneration effects (>50%) for all systems. Cocktails containing O had high regeneration effects for MAb 609 only. Also, r154 and r200 were regenerated close to completely by ICw and AIw, but were not especially affected by ADw, in contrast to g3_clone2 for which ICw, Aw and ADw all had high $R_e$.

Figure 12:
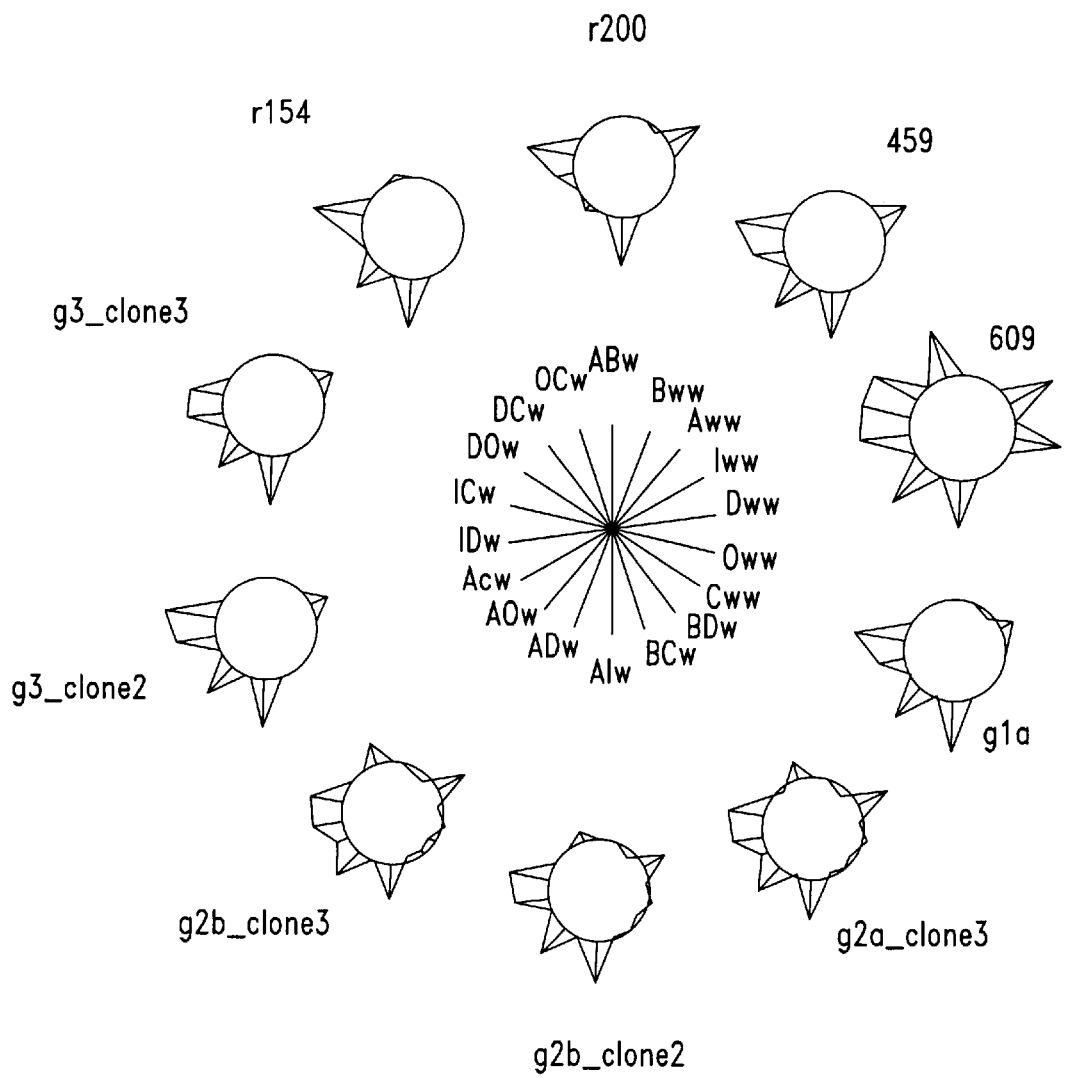
FIG. 12 illustrates the measured $R_e$ values for a plurality of screening cocktails tested on a biosensor having a bound ligand, SpA, with the following MAb analytes: g3_clone2, g3_clone3, g2b_clone2, g2b _clone3, g2a, g1a, anti-theofyllin MAb 459, anti-p24 MAb 609, polyclonal anti-clenbuterol Abs r200 and r154.

As for characterization of the analytes, the regeneration pattern illustrated in FIG. 12 may be used as a unique identification or "finger print"for each of the tested analytes. Such characterization may be used to predict the functionality of other analytes by comparison to a predetermined, test library of known molecules. For example, another MAb which exhibits similar characteristics to one (or more) of the above-tested MAbs would be expected to have similar activity to the known MAb. Such characterization has utility over a wide range of applications, including (but not limited to) drug identification and/or optimization, quantitative assays, as well as epitope mapping.

Discussion of Results

The RO-protocol of the present invention is an extremely valuable tool for identifying and optimizing regeneration conditions that withhold full ligand activity, have high regeneration effect, offer quick recover to a stable baseline and work with short contact time. All experiments in the RO-protocol were designed to identify at least one cocktail that works. The RO-protocol of the present invention has several advantages over conventional regeneration optimization techniques. The protocol is based on multivariate experimental design which ensures maximal variation of the parameters under investigation as well as ease-of-use both regarding screening cocktail preparation and result evaluation. A validation of the regeneration results is also obtained by testing all cocktails in the design even if one is identified as possible regeneration agent early in the run. This is exemplified in FIG. 9, where the complete result plot reveals that all three components are necessary, although the components influence to different extents.

The regeneration stock solutions were chosen with maximal diversity as primary goal. Most commonly used regeneration conditions can be obtained with cocktails of the stocks. The risk of damaging the ligand is low due to the gentle screening cocktails. The time spent for regeneration optimization is decreased, primarily because of the multivariate approach. In automated mode, the screening session may take 3–8 hours, depending on the biomolecular-interaction system. Most important of all, the RO-protocol of the present invention works under true-laboratory conditions. The RO-protocol identified regeneration cocktails for many systems already in the first screening session. In two cases, an optimization was performed to identify suitable regeneration cocktail. The cocktail was optimized primarily towards 100% regeneration and secondly towards a quick return to a stable baseline. Furthermore, the RO-protocol provided a "map" over the system behavior for different regeneration conditions. This map can be very useful to start the manual investigation of regeneration conditions from if the RO-protocol cocktails fails to regenerate the surface. Furthermore, the screening cocktails can easily be made more concentrated by reducing the 33–67 volume percent water to 0–33% in all cocktails.

Previous work by van Oss (In *Immunochemistry*, van Oss and Regenmortel (Eds), Marcel Dekker, New York, 1994) indicates that combinations of agents of different kinds are preferable for breaking the binding between antibodies and antigens, especially combinations of agents affecting the interactions between Lewis acids and Lewis bases (L) and electrostatic forces (E). For example, drastic pH decrease affecting mainly E combined with unpolar solvents affecting mainly L is a good regeneration agent in many cases. In the RO-protocol, such combinations are tested, but with two major differences compared to previous work: first, several different agents with similar main properties were used instead of combining one solvent with one acid/base; and, second, the combinations were chosen with a multivariate approach which minimizes the risk of missing relevant combinations of agents.

The above experiments illustrate that the cocktail approach used in the RO-protocol is successful. Several completely different cocktails had high $R_e$ for some investigated systems. Also, the cocktails influenced the dissociation of the investigated systems to different extents. Collection of results for several systems show that multi-stock cocktails have significantly higher regeneration effects than single-stock cocktails. The screening cocktail AIw was expected to have better regeneration effects than Aww and Iww. The multivariate approach used in the RO-protocol revealed that another cocktail, ICw, had significantly higher $R_e$ than those of the single diluted stocks Iww and Cww. The excellent regeneration properties of ICw was completely unexpected. This unexpected result exemplifies the strength of multivariate experimental design.

The sensorgrams must be evaluated correctly in order to give relevant information. Occasionally, matrix effects influences the sensorgram for several minutes. Most matrix effects are due to protein folding, but occasionally other mechanisms influences the matrix as well. The loss of detergents adsorbed to the surface and the use of the unpolar stock are two such examples. Carryover effects were prevented by extensive washes after each cocktail injection. Normally, signals due to different artifacts are transient and disappear within 60 seconds, with the exception of the detergent adsorption. It is important to learn to distinguish between true dissociation and signals due to artifacts. In the RO-protocol sensorgrams this is quite simple since systems with fast dissociation are unlikely to be subject to a regeneration investigation. Moreover, since an analyte injection was performed after each successful cocktail the surface status was continuously monitored.

When the analyte is a polyclonal antibody, the interpretation of the data may become more difficult. The $R_e$ value will be too large when it is determined immediately after an analyte injection, and too low after a few analyte injections performed on incompletely regenerated surfaces. In spite of the difficulties in data interpretation and the low $R_e$ measured for the screening cocktails, only one optimization experiment was needed to identify a cocktail that regenerated the surface completely.

The ligand can also influence the signal in a confusing way. Some ligands need a few regeneration pulses to stabilize, which makes the determination of reference baseline difficult. This made the first few measured $R_e$ values on some new surfaces less reliable. The suspiciously high $R_e$ value 114 in the GST-antiGST optimization was probably due to such a baseline decrease. Negative $R_e$ values also appear. These were probably due to matrix effects.

The simple evaluation plots, such as FIGS. 10 and 11, monitor trends in the behavior of $R_e$ in a clear way. If the results from a session are unsatisfactory, the evaluation plot indicates which new stocks proportions that are favorable. Thus, the RO-protocol is a great help even if complete regeneration is not obtained. The visual evaluation also simplifies the identification of erroneous results ("outliers").

The RO-protocol identified two interesting combination effects which both seemed to be general. First, regeneration cocktail IOw was unexpectedly found to be too aggressive. Second, the stock I and C alone are significantly less good as regeneration agents than the cocktail IC. The only difference between the two solutions is the 6.7 mM EDTA present in the latter solution. It should be noted that $[Mg^{2+}]$= 610 mM, which means that the EDTA-molecules are complexed with a Mg ion. Thus, the $Mg^{2+}$-EDTA complex, possibly in combination with either or both of the chaotropic agents GuHCl and urea and the SCN—ion, increases dissociation significantly. The optimization experiment for the GST system show that the effect of EDTA as additive was better at lower pH.

The results from the SpA experiments show that systems with one ligand and different analytes behave differently when the RO-protocol is applied to the systems. For example, only one system, SpA MAb 609, was affected by the cocktails Uww and UCw.

From the foregoing, it will be understood that, although specific embodiments of this invention have been described herein for purposes of illustration, various modifications may be made without departing from the spirit and scope of the invention. Accordingly, the invention is not limited except by the appended claims.

What is claimed is:

1. A method for selecting an optimized regeneration solution for the regeneration of a biosensor surface having a surface-bound ligand and an analyte associated with the ligand, comprising:

(a) sequentially contacting the biosensor surface with each of a plurality of first regeneration cocktails, wherein each of said first regeneration cocktails is an aqueous solution comprising at least one acidic, basic, ionic, organic, detergent or chelating stock solution, and wherein at least one of said first regeneration cocktails comprises a mixture of at least two of said stock solutions;

(b) measuring the regeneration effect for each of said plurality of first regeneration cocktails to determine which of said plurality of first regeneration cocktails have the highest measured regeneration effect;

(c) selecting at least two different stock solutions present in said plurality of first regeneration cocktails having the highest measured regeneration effect;

(d) combining said at least two different stock solutions in various ratios to generate a plurality of second regeneration cocktails;

(e) sequentially contacting the biosenor surface with each of said plurality of second regeneration cocktails; and (f) determining the regeneration effect of each of said plurality of second regeneration cocktails and therefrom identifying a second regeneration cocktail as the optimized regeneration solution.

2. The method of claim 1 wherein, during the step of sequentially contacting the biosensor surface with each of said plurality of first regeneration cocktails, the biosensor surface is contacted with an additional quantity of analyte to associate said additional quantity of analyte with the surface-bound ligand.

3. The method of claim 1 wherein the ligand and analyte are a binding pair selected from antibody-antigen, hormone-hormone receptor, polynucleotide-complementary polynucleotide, avidin/streptavidin-biotin, enzyme-enzyme substrate or inhibitor, lectins-specific carboxyhydrate, lipids-lipid binding proteins or membrane-associated proteins, polynucleotides-polynucleotide binding proteins, receptor-transmitter, drug-target, protein-protein, protein-polynucleotide, DNA-DNA, and DNA-RNA.

4. The method of claims 1 wherein the ligand is an antibody and the analyte is an antigen.

5. The method of claim 1 wherein said mixture of at least two of said stock solutions is selected from a mixture of basic and acidic stock solutions, basic and detergent stock solutions, basic and chelating stock solutions, acidic and ionic stock solutions, acidic and nonpolar stock solutions, acid and detergent stock solutions, acid and chelating stock solutions, ionic and detergent stock solutions, ionic and chelating stock solutions, detergent and nonpolar stock solutions, detergent and chelating stock solutions, and nonpolar and chelating stock solutions.

6. The method of claim 1 wherein said plurality of first regeneration cocktails are aqueous solutions containing an acidic stock solution, a basic stock solution, an ionic stock solution, a nonpolar stock solution, a detergent stock solution, a chelating stock solution, a mixture of basic and acidic stock solutions, a mixture of basic and detergent stock solutions, a mixture of basic and chelating stock solutions, a mixture of acidic and ionic stock solutions, a mixture of acidic and nonpolar stock solutions, a mixture of acid and detergent stock solutions, a mixture of acid and chelating stock solutions, a mixture of ionic and detergent stock solutions, a mixture of ionic and chelating stock solutions, a mixture of detergent and nonpolar stock solutions, a mixture of detergent and chelating stock solutions, and a mixture of nonpolar and chelating stock solutions.

7. The method of claim 1 wherein said acidic stock solution comprises a mixture of acids having dispersed pKs ranging from about 2 up to 7.

8. The method of claim 7 wherein said acidic stock solution has a pH ranging from 1 up to 7.

9. The method of claim 7 wherein said acidic stock solution is a mixture of acids comprising at least two acids selected from arsenic acid, arsenious acid, o-boric acid, carbonic acid, chromic acid, germanic acid, hyrocyanic acid, hydrofluoric acid, hydrogen sulfide, hydrogen peroxide, hypobromus acid, hypochlorous acid, hypoiodous acid, iodic acid, nitrous acid, periodic acid, o-phosphoric acid, phosphorous acid, pyrophosphoric acid, selenic acid, selenious acid, m-silic acid, o-silic acid, sulfuric acid, sulfurous acid, telluric acid, tellurous acid, tetraboric acid, acetic acid, acetoacetic acid, acrylic acid, adipamic acid, adipic acid, d-alanine, allantoin, alloxanic acid, glycine, o-aminobenzoic acid, m-aminobenzoic acid, p-aminobenzoic acid, o-aminobenzsulfonic acid, m-aminobenzsulfonic acid, p-aminobenzsulfonic acid, ainsic acid, o-beta-anisylpropionic acid, m-beta-anisylpropionic acid, p-beta-anisylpropionic acid, ascorbic acid, DL-aspartic acid, barbituric acid, benzoic acid, benzosoulfonic acid, bromoacetic acid, o-bromobenzoic acid, m-bromobenzoic acid, n-butyric acid, iso-butyric acid, cyclopropane-1:1-dicarboxylic acid, DL-cystein, L-cystein, dichloroacetic acid, dichloroacetylacetic acid, 2,3-dichlorophenol, 2,2-dihydroxybenzoic, 2,5-dihydroxybenzoic, 3,4-dihydroxybenzoic, 3,5-dihydroxybenzoic, dihydroxymalic acid, dihydroxytartaric acid, dimethylglycine, dimethylmalic acid, dimethylmalonic acid, dinicotinic acid, 2,4-dinitrophenol, 3,6-dinitrophenol, diphenylacetic acid, ethylbenzoic acid, ethylphenylacetic acid, fluorobenzoic acid, formic acid, fumaric acid, furancarboxylic acid, furoic acid, cacodylic acid, n-caproic acid, iso-caproic acid, chloroacetic acid, o-chlorobenzoic acid, m-chlorobenzoic acid, p-chlorobenzoic acid, o-chlorobutyric acid, m-chlorobutyric acid, p-chlorobutyric acid, o-chloroinnamic acid ,m-chloroinnamic acid, p-chloroinnamic acid, o-chlorophenoxyacetic acid, m-chlorophenoxyacetic acid, p-chlorophenoxyacetic acid, o-chlorophenylacetic acid, m-chlorophenylacetic acid, p-chlorophenylacetic acid, beta-(o-chlorophenyl) propionic acid, beta-(m-chlorophenyl) propionic acid, beta-(p-chlorophenyl) propionic acid, alfa-chloropropinic acid, beta-chloropropionic acid, cis-cinnamic acid, trans-cinnamic acid, citric acid, o-cresol, m-cresol, p-cresol, trans-crotonic acid, cyanoacetic acid, gamma-cyanobutyric acid, o-cyanophenoxyacetic acid, p-cyanophenoxyacetic acid, cyanopropionic acid, cycloheaxane-1:1-dicarboxylic acid, gallic acid, glutamaric acid, glutaric acid, glycerol, glycine, glycol, glycolic acid, heptanoic acid, hexahydrobenzoic acid, hexanoic acid, hippuric acid, histidine, hydroquinone, o-hydroxybenzoic acid, m-hydroxybenzoic acid, p-hydroxybenzoic acid, beta-hydroxybutyric acid, gamma-hydroxybutyric acid, beta-hydroxypropionic acid, gamma-hydroxyquinoline, iodoacetic acid, o-iodobenzoic acid, m-iodobenzoic acid, itaconic acid, lactic acid, lutidinic acid, lysine, maleic acid, malic acid, malonic acid, DL-mandelic acid, mesaconic acid, mesitylenic acid, methyl-o-aminobenzoic acid, methyl-m-aminobenzoic acid, methyl-p-aminobenzoic acid, o-methylcinnamic acid, m-methylcinnamic acid, p-methylcinnamic acid, beta-methylglutaric acid, n-methylglycine, methylmalonic acid, methylsuccinic acid, o-monochlorophenol, m-monochlorophenol, p-monochlorophenol, o-phthalic acid, m-phthalic acid, p-phthalic acid, picric acid, pimelic acid, propionic acid, iso-propylbenzoic acid, 2-pyridinecarboxylic acid, 3-pyridinecarboxylic acid, 4-pyridinecarboxylic acid, pyrocatcchol, quinolinic acid, Resorcinol, Saccarin, suberic acid, succinic acid, sulfanilic acid, naphtalenesulfonic acid, alfa-naphthoic acid, beta-naphthoic acid, alfa-napthol, beta-napthol, nitrobenzene, o-nitrobenzoic acid, m-nitrobenzoic acid, p-nitrobenzoic acid, o-nitrophenol, m-nitrophenol, p-nitrophenol, o-nitrophenylacetic acid, m-nitrophenylacetic acid, p-nitrophenylacetic acid, o-beta nitrophenylpropionic acid, p-beta nitrophenylpropionic acid, nonanic acid, octanic acid, oxalic acid, phenol, phenylacetic acid, o-phenylbenzoic acid, gamma-phenylbutyric acid, alfa-phenylpropionic acid, beta-phenylpropionic acid, alfa-tataric acid, alfa-tartaric acid, meso-tartaric acid, theobromine, terephtalic acid, thioacetic acid, thiophenecarboxylic acid, o-toluic acid, m-toluic acid, p-toluic acid, trichloroacetic acid, trichlorophenol, 2,4,6-trihydroxybenzoic acid, trimethylacetic acid, 2,4,6-trinitrophenol, tryptophan, tyrosine, uric acid, n-valeric acid, iso-valeric acid, veronal, vinylacetic acid, and xanthine.

10. The method of claim 7 wherein said acidic stock solution is a mixture of acids comprising oxalic, phosphoric, formic and malonic acid.

11. The method of claim 1 wherein said basic stock solution comprises a mixture of bases having dispersed pKs ranging from in excess of 7 up to about 12.

12. The method of claim 11 wherein said basic stock solution is a mixture of bases comprising at least two bases selected from acetamide, acridin, alfa-alanin, gylcyl alanin, methoxy (DL)-alanin, phenyl alanin, allothreonin, n-amylamine, aniline, n-allyl aniline, 4-(p-aminobenzoyl) aniline, 4-benzyl aniline, 2-bromo aniline, 3-bromo aniline, 4-bromo aniline, 4-bromo-N,N,dimethyl aniline, o-chloro aniline, m-chloro aniline, p-chloro aniline, 3-bromo-N,N, dimethyl aniline, 4-bromo-N,N,dimethyl aniline, 3,5-dibromo Aniline, 2,4-dichloro aniline, N,N-diethyl aniline, N,N-dimethyl-3-nitro aniline, N-ethyl aniline, 2-fluoro aniline, 3- fluoro aniline, 4- fluoro aniline, 2-iodo aniline, N-methyl aniline, N-methylthio aniline, 3-nitro aniline, 4-nitro aniline, 2-sulfonic acid aniline, 3-sulfonic acid aniline, 4-sulfonic acid aniline, brucine, 1-amino-3-methyl-butane, 2-amino-4-methyl-butane, 1,4-diamino-butane, n-butylamine, t-butylamine, 4-amino butyric acid, lycyl-2-amino n-butyric acid, cacodylic acid, beta-chlortriethylammonium, cinnoline, codeine, n-butyl-cyclohexanamin, cyclohexanamin, cystin, n-decylamine, diethylamine, diisobutylamine, diisopropylamine, dimethylamine, n-diphenylamine, n-dodecaneamine, d-ephedrine, 1-ephedrine, 1-amino-3-metoxy-ethane, 2-amino ethanole, o-anisidine, m-anisidine, p-anisidine, arginin, asparagin, glycylasparagin, DL-aspartic acid, azetidin, aziridine, 4-aminoazo benzene, 2-aminoethyl benzene, 4-dimethylaminoazo benzene, benzidine, benzimidazole, 2-ethyl benzimidazole, 2-methyl benzimidazole, 2-phenyl benzimidazole, 2-amino benzoic acid, 4-amino benzoic acid, benzylamine, betaine, 2-amino biphenyl, trans-bomylamine, ehtylamine, ethylenediamine, 1-Glutamic acid, alfa-monoethyl glutamic acid, 1-glutamine, 1-glutathione, glycine, n-acetyl glycine, dimethyl glycine, glycyl glycine, glycylglycyl glycine, leucyl glycine, methyl glycine, phenyl glycine, N,n-propyl glycine, tetraglycyl glycine, glycylserine, hexadecanamine, 1-amino heptan, 2-amino-heptan, 2-metylamino heptan, hexadecanamine, hexamethylenediamine, 6-amino hexanoic acid, n-hexylamine, dl-histidine, beta-analyl histidine, imidazol, 2,4-dimethyl imidazol, 1-methyl imidazol, 1-amino indane, 2-amino isobutyric acid, isoleucin, isoquinolin, 1-amino isoquinolin, 7-hydroxy isoquinolin, L-leucin, glycyl leucin, methionin, metylamine, morphine, morpholine, 1-amino-6-hydroxy naphtalene, dimethylamino naphtalene, alfa-naphthylamine, beta-napthylamine, piperazine, 2,5,dimetyl(trans)piperazine, piperidine, 3-acetyl piperidine, 1-n-butyl piperidine, 1,2-dimethyl piperidine, 1-ethyl piperidine, 1-methyl piperidine, 2,2,6,6, tetramethyl piperidine, 2,2,4-trimethyl piperidine, proline, hydroxyproline, 1-amino-2,2-dimethylpropane, 1,2-diaminopropane, 1,3-diaminopropane, 1,2,3-triaminopropane, 3-amino propanoic acid, propylamine, pteridine, 2-amino-4-hydroxy pteridine, 2-amino-4,6-dihydroxy pteridine, 6-chloro pteridine, 6-hydroxy-4-methyl pteridine, purine, n-methyl alfa-naphtylamine, cis-neobornylamine, nicotine, n-nonylamine, norleucine, octadecanamine, octylamine, omithine, papaverine, 3-amino pentane, 3-amino-3-methyl pentane, n-pentadecylamine, 5-amino pentanoic acid, perimidine, phenanthridine, 1,10-phenanthroline, o-phenetidine, m-phenetidine, p-phenetidine, alfa-picoline, beta-picoline, gamma-picoline, pilocarpine, 6-amino purin, 2-dimethylaminopurine, 8-hydroxy purin, pyrazin, 2-methylpyrazine, methylaminopyrazine, pyrdazine, 2-aminopyrimidine, 2-amino-4,6-dimethylpyrimidine, 2-amino-5-nitro pyrimidine, pyridine, 2-amino pyridine, 4-amino pyridine, 2-benzyl pyridine, 3-bromo pyridine, 3-chloro pyridine, 2,5-diamino pyridine, 2,3-dimethyl pyridine, 2,4-dimethyl pyridine, 2-ethyl pyridine, 2-formyl pyridine, a-hydroxy pyridine, 4-hydroxy pyridine, methoxy pyridine, 4-methylamino pyridine, 2,4,6,trimetyl pyridine, pyrrolidine, 1,2-dimethyl pyrrolidine, n-methyl pyrrolidine, quinazoline, 5-hydroxy quinazoline, quinine, quinoline, 3-amino quinoline, 3-bromo quinoline, 8-carboxy quinoline, 3-hydroxy quinoline, 8-hydroxy quinoline, 8-hydroxy-5-sulfo quinoline, 6-methoxy quinoline, 2-methyl quinoline, 4-methyl quinoline, 5-methyl quinoline, quinoxaline, serine, strychnine, taurine; tetradecaneamin, thiazole, 2-aminothiazole, threonine, o-toluidine, m-toluidine, p-toluidine, 2,4,6-triamino-1,3,5-triazine, tridecanamine, triethylamine, trimethylamine, tryptophan, tyrosine, urea, valine, ammonium hydroxide, arsenous oxide, beryllium hydroxide, calcium hydroxide, deuteroammonium hydroxide, hydrazine, hydroxylamine, lead hydroxide, silver hydroxide, and zinc hydroxide.

13. The method of claim 11 wherein said basic stock solution is a mixture of bases comprising ethanolamine, sodium phosphate, piperazin and glycine.

14. The method of claim 1 wherein said ionic stock solution comprises a mixture of at least two ions selected from $PO_4^{3-}$, $SO_4^{2-}$, $CH_3COO-$, $Br-$, $NO_3-$, $NO_2-$, $ClO_4-$, $Cl-$, $F-$, $I-$, $CF_3COO-$, $SCN-$, $Cl_3COO-$, $CCl_3COO-$, $(CH_3)_4N^+$, $NH_4^+$, $Rb^+$, $K^+$, $Na^+$, $Cs^+$, $Li^+$, $Mg^{2+}$, $Ca^{2+}$, $Sr^{2+}$, and $Ba^{2+}$.

15. The method of claim 14 wherein said ionic stock solution comprises potassium thiocyanate, magnesium chloride, urea and guanidine HCl.

16. The method of claim 1 wherein said organic stock solution comprises a mixture of at least two organic solvents selected from DMSO, formamide, ethanol, acetonitrile, 1-butanol, acetone, methyl acetate, dichloroethane, chloroform, methyl alcohol, tetrahydrofuran, n-hexane, diisopropyl ether, ethyl acetate, ethyl alcohol, butanone, n-hexane, 2-propanol, 1,2-dichloroethane, flourobenzene, acetone, trichloroethylene, triethylamine, 1-propanol, butyronitrile, 2-butanol, nitromethane, dioxane, 2,2-dimethylpropanole, 3-pentanone, piperazine, 3-propanol, pyridin, 1-butanol, acetic acid, 2-metoxy ethanol, 3-methyl-1-butanol, chlorobenzene, acetic anhydride, dimethylformamide, methoxybenzene, methylbutylketone, bromobenzene, 1-hexanol, n-methyl formamide, aniline, iodobenzene, glycol, phenyl acetate, n-methyl formamide, benzyl alcohol, formamide, nitrophenol, diethyleneglycol, diphenylether, sulfolan, diethylether, methylene chloride, carbon disulfide, carbon tetrachloride, benzene, acetonitrile, toluene, dibutyl ether, dimethylbenzene, ortho-dichlorobenzene, and benzonitrile.

17. The method of claim 16 wherein said nonpolar stock solution comprises DMSO, formamide, ethanol, acetonitrile and 1-butanol.

18. The method of claim 1 wherein said detergent stock solution comprises a mixture of at least two detergent agents selected from anionic detergents, cationic detergents, zwitterionic detergents, and nonionic detergents.

19. The method of claim 18 wherein said detergent stock solution comprises CHAPS, Zwittergent 3–12, tween 80, tween 20 and triton X-100.

20. The method of claim 1 wherein said chelating stock solution comprises at least one chelating agent selected from EDTA, EGTA, NTA, DCYTA, GLEDTA, ETHEDTA, IDA and crown ethers.

21. The method of claim 20 wherein said chelating stock solution comprises EDTA.

22. The method of claim 1 wherein each of said stock solutions contains at least 20 mM of each individual component present within said stock solution.

23. The method of claim 1 wherein each of said plurality of first regeneration cocktails contains a relative volume ratio of water to total stock solution in an amount ranging from 2:1 to 1:2.

24. The method of claim 1 wherein the biosensor surface has a gold layer thereon which is capable of supporting surface plasmon resonance, and wherein the ligand is bound directly or indirectly to the gold layer.

25. The method of claim 4 wherein a dextran matrix is bound to the gold layer and the ligand bound to the dextran matrix.

26. The method of claim 1 wherein said at least two different stock solutions are two different stock solutions.

27. The method of claim 1 wherein said at least two different stock solutions are three different stock solutions.

28. The method of claim 1 wherein said at least two different stock solutions are four different stock solutions.

29. The method of claim 1, further comprising, after step (f):
(g) combining said at least two different stock solutions in different ratios than step (d) to generate a plurality of third regeneration cocktails;
(h) sequentially contacting the biosensor surface with each of said plurality of third regeneration cocktails; and
(i) determining the regeneration effect of each of said plurality of third regeneration cocktails and therefrom identifying a third regeneration cocktail as the optimized regeneration solution.

30. The method of claim 29 wherein steps (f) through (h) yields an optimized regeneration solution having a higher regeneration effect than the optimized regeneration solution identified in step (e).

31. The method of claim 1, further comprising:
(g) collecting the analyte for subsequent analysis.

32. A reagent kit comprising at least two different stock solutions for use in the method of claim 1 wherein said stock solutions are selected from an acidic stock solution, a basic stock solution, an ionic stock solution, an organic stock solution, a detergent stock solution and a chelating stock solution.

33. The reagent kit of claim 32 comprising at least three different stock solutions.

34. The reagent kit of claim 32 comprising four to five different stock solutions.

35. The reagent kit of claim 32 comprising six different stock solutions.

36. A method for using stored instructions in a computer for selecting an optimized regeneration solution for the regeneration of a biosensor surface having a surface-bound ligand and an analyte associated with the ligand, comprising:
instructing a device to combine a series of stock solutions in various ratios to generate a plurality of first regeneration cocktails,
sequentially controlling the device to contact the biosensor surface with each of said plurality of first regeneration cocktails;
determining the regeneration effect of each of said first regeneration cocktails on the biosensor surface based on measurements received from the device;
selecting at least two different stock solutions having the highest regeneration effect;
instructing the device to combine a subset of said at least two different stock solutions in varying ratios to generate a plurality of second regeneration cocktails;
sequentially controlling the device to contact the biosensor surface with each of said second regeneration cocktails; and
determining the regeneration effect of each of said second regeneration cocktails based on measurements received from the device, and therefrom identifying a second regeneration cocktail as the optimized regeneration solution.

37. A computer-readable medium containing instructions for performing the method of claim 36.

38. A method for characterizing a ligand or analyte associated with a biosensor surface, comprising the steps of:
(a) sequentially contacting the biosensor surface having a surface-bound ligand with each of a plurality of characterization solutions;
(b) introducing the analyte into each of said plurality of characterization solutions so as to interact the analyte with the surface-bound ligand;
(c) measuring at least one of an association rate, surface-bound analyte concentration, dissociation rate, and regeneration effect of the analyte-ligand interaction for each of said plurality of characterization solutions; and
(d) characterizing the ligand or analyte associated with the biosensor surface based on at least one of the association rate, surface-bound analyte concentration, dissociation rate, and regeneration effect of the analyte-ligand interaction for each of said plurality of characterization solutions.

39. The method of claim 38, further comprising, after step (d):
(e) comparing the characterization of the ligand and/or analyte associated with the biosensor surface with a set of predetermined characterizations of other test molecules and thereby predicting the activity thereof.

40. The method of claim 39 wherein the set of predetermined characterizations of other test molecules includes a plurality of analogues of the ligand or analyte.

41. The method of claim 38 wherein each of said characterization solutions is an aqueous solution comprising at least one acidic, basic, ionic, organic, detergent or chelating solution.

42. The method of claim 41 wherein each aqueous solution is a single component solution.

43. The method of claim 41 wherein at least one of said characterization solutions comprises a mixture of at least two stock solutions.

44. The method of claim 41 wherein said plurality of characterization solutions are aqueous solutions selected from an acidic stock solution, a basic stock solution, an ionic stock solution, a nonpolar stock solution, a detergent stock solution, a chelating stock solution, a mixture of basic and acidic stock solutions, a mixture of basic and detergent stock solutions, a mixture of basic and chelating stock solutions, a mixture of acidic and ionic stock solutions, a mixture of acidic and nonpolar stock solutions, a mixture of acid and detergent stock solutions, a mixture of acid and chelating stock solutions, a mixture of ionic and detergent stock solutions, a mixture of ionic and chelating stock solutions, a mixture of detergent and nonpolar stock solutions, a mixture of detergent and chelating stock solutions, and a mixture of nonpolar and chelating stock solutions.

45. The method of claim 41, further comprising, after step (d):

(e) using a mathematical model wherein a structure of the analyte or ligand is given for predicting the activity of the analyte or ligand.

46. The method of claim 45 wherein the mathematical model uses pattern recognition algorithms.

47. The method of claim 41 wherein characterizing the ligand or analyte associated with the biosensor surface based on at least one of the association rate, surface-bound analyte concentration, dissociation rate, and regeneration effect of the analyte-ligand interaction for each of said plurality of characterization solutions comprises:

using a mathematical model having properties for determining a biospecific interaction effect of the analyte or ligand.

48. The method of claim 38 wherein the plurality of characterization solutions are at at least two different temperatures.

* * * * *